US012264208B2

(12) United States Patent
Baxter, Jr. et al.

(10) Patent No.: US 12,264,208 B2
(45) Date of Patent: *Apr. 1, 2025

(54) PROCESSES FOR CONVERTING C4 FEEDS TO ISOBUTYLENE, POLYISOBUTYLENE, OR DERIVATIVES THEREOF

(71) Applicant: NTP Tec, LLC, Boerne, TX (US)

(72) Inventors: Clyde Edward Baxter, Jr., League City, TX (US); Mark W. Roll, Boerne, TX (US); Billy W. Waycaster, Cypress, TX (US)

(73) Assignee: NTP Tec, LLC, Boerne, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/829,679

(22) Filed: Sep. 10, 2024

(65) Prior Publication Data
US 2024/0425624 A1 Dec. 26, 2024

Related U.S. Application Data

(63) Continuation of application No. 18/661,249, filed on May 10, 2024.

(60) Provisional application No. 63/630,397, filed on Jan. 31, 2024, provisional application No. 63/629,098, filed on Sep. 20, 2023, provisional application No. 63/577,757, filed on May 19, 2023.

(51) Int. Cl.
*C08F 10/10* (2006.01)
*C07C 5/27* (2006.01)

(52) U.S. Cl.
CPC ............ *C08F 10/10* (2013.01); *C07C 5/2767* (2013.01)

(58) Field of Classification Search
CPC .................. C08F 10/10; C07C 5/2767
See application file for complete search history.

(56) References Cited

U.S. PATENT DOCUMENTS

| | | | |
|---|---|---|---|
| 1,885,060 A | 10/1932 | Hoffmann et al. | |
| 2,404,788 A | 7/1946 | Burk et al. | |
| 2,484,384 A | 10/1949 | Levine et al. | |
| 2,552,692 A | 5/1951 | Schulze et al. | |
| 2,677,002 A | 4/1954 | Yahnke et al. | |
| 2,721,889 A | 10/1955 | O'Young et al. | |
| 2,766,312 A | 10/1956 | Serniuk et al. | |
| 2,804,411 A | 8/1957 | Anderson et al. | |
| 2,804,491 A | 8/1957 | May et al. | |
| 2,957,930 A | 10/1960 | Jackson et al. | |
| 2,976,338 A | 3/1961 | Thomas | |
| 3,068,301 A | 12/1962 | Hervert et al. | |
| 3,114,785 A | 12/1963 | Hervert et al. | |
| 3,119,884 A | 1/1964 | Allen et al. | |
| 3,131,156 A | 4/1964 | Grace | |
| 3,131,320 A | 4/1964 | Shinada et al. | |
| 4,152,499 A | 5/1979 | Boerzel et al. | |
| 4,256,913 A | 3/1981 | Jung et al. | |
| 4,306,105 A | 12/1981 | Abernathy et al. | |
| 4,400,565 A | 8/1983 | Darden et al. | |
| 4,407,731 A | 10/1983 | Imai | |
| 4,409,410 A * | 10/1983 | Cosyns | C07C 5/03 585/843 |
| 4,427,791 A | 1/1984 | Miale et al. | |
| 4,427,797 A | 1/1984 | Smith | |
| 4,427,941 A | 1/1984 | Riedesel, Jr. et al. | |
| 4,429,177 A | 1/1984 | Morganson et al. | |
| 4,533,651 A | 8/1985 | Masters et al. | |
| 4,558,168 A | 12/1985 | Gussow et al. | |
| 4,605,808 A | 8/1986 | Samson | |
| 4,707,731 A | 11/1987 | Ghazey | |
| 4,915,255 A | 4/1990 | Curtis | |

(Continued)

FOREIGN PATENT DOCUMENTS

| | | |
|---|---|---|
| CA | 2866897 A1 | 12/2013 |
| WO | 9402243 A1 | 2/1994 |

(Continued)

OTHER PUBLICATIONS

Lamprecht et al., Hydroisomerization of 1-pentene to isopentane in a Single Reactor, May 12, 2009, vol. 196, pp. 1206-1216, (Year: 2009).*
Komatsu et al., Dehydroisomerization of butane into isobutene on Pt—Sn intermetallic compounds supported on H-SAPO-11, Journal of Catalysis, 241 (2006), pp. 426-434 (Year: 2006).*
Wilson, Karen et al., "Synthesis of a Supported Solid Acid BF3 Catalyst", J. of Chem. Soc., Chem. Commun., 1998, pp. 2135-2136.
Canadian Office Action for Application No. CA 3,053,389 dated Sep. 9, 2020.
Indian Office Action for Application No. IN 201947036946 dated Oct. 14, 2020.
Extended European Search Report dated Jan. 28, 2021 for Application No. 18758114.5.

(Continued)

*Primary Examiner* — Robert D Harlan
(74) *Attorney, Agent, or Firm* — Patterson + Sheridan, LLP

(57) ABSTRACT

Embodiments described herein generally relate to new processes for converting C4 feeds to isobutylene. In an embodiment is provided a process for forming isobutylene that includes hydroisomerizing 1,3-butadiene present in a C4 feed to form a hydroisomerization product effluent comprising isobutylene and 2-butene; and forming an isobutylene feed by separating the isobutylene from the hydroisomerization product effluent. Embodiments of the present disclosure also generally relate to new processes for converting C4 feeds to polyisobutylene. In an embodiment is provided a process that includes hydroisomerizing a C4 feed comprising 1,3-butadiene in a hydroisomerization reactor to form a hydroisomerization product effluent comprising isobutylene and 2-butene; separating the isobutylene from the hydroisomerization product effluent to form a first isobutylene-containing feed; forming a reaction mixture comprising a polymerization catalyst and the first isobutylene-containing feed; and reacting the reaction mixture, in a polymerization reactor, to form a polymerization product effluent comprising polyisobutylene.

19 Claims, 4 Drawing Sheets

(56) References Cited

U.S. PATENT DOCUMENTS

| | | |
|---|---|---|
| 4,918,255 A | 4/1990 | Chou et al. |
| 4,935,577 A | 6/1990 | Huss, Jr. et al. |
| 5,068,487 A | 11/1991 | Theriot |
| 5,068,490 A | 11/1991 | Eaton |
| 5,191,044 A | 3/1993 | Rath et al. |
| 5,268,520 A | 12/1993 | Karn et al. |
| 5,286,823 A | 2/1994 | Rath |
| 5,294,578 A | 3/1994 | Ho et al. |
| 5,300,701 A | 4/1994 | Cherpeck |
| 5,326,920 A | 7/1994 | Ho et al. |
| 5,326,923 A | 7/1994 | Cooper et al. |
| 5,408,018 A | 4/1995 | Rath |
| 5,408,108 A | 4/1995 | Nakamura et al. |
| 5,510,560 A | 4/1996 | O'Young et al. |
| 5,646,332 A | 7/1997 | Cusumano et al. |
| 5,663,470 A | 9/1997 | Chen et al. |
| 5,710,225 A | 1/1998 | Johnson et al. |
| 5,770,539 A | 6/1998 | Chen et al. |
| 5,789,335 A | 8/1998 | Chen et al. |
| 5,877,365 A * | 3/1999 | Chodorge ............... C07C 6/04 585/329 |
| 5,910,550 A | 6/1999 | Rath |
| 5,945,575 A | 8/1999 | Sigwart et al. |
| 5,962,604 A | 10/1999 | Rath |
| 6,207,115 B1 | 3/2001 | Chodorge et al. |
| 6,294,578 B1 | 9/2001 | Arimoto et al. |
| 6,384,054 B1 | 5/2002 | Woosley et al. |
| 6,384,154 B1 | 5/2002 | Sigwart et al. |
| 6,433,238 B1 | 8/2002 | Di Girolamo et al. |
| 6,441,110 B1 | 8/2002 | Sigwart et al. |
| 6,525,149 B1 | 2/2003 | Baxter, Jr. et al. |
| 6,562,013 B1 | 5/2003 | Marasco, Jr. |
| 6,562,913 B1 | 5/2003 | Baxter, Jr. et al. |
| 6,683,138 B2 | 1/2004 | Baxter, Jr. et al. |
| 6,686,510 B2 * | 2/2004 | Commereuc ........... C07C 7/163 585/324 |
| 6,710,140 B2 | 3/2004 | Wettling et al. |
| 6,867,267 B2 | 3/2005 | Lewtas et al. |
| 6,884,858 B2 | 4/2005 | Baxter, Jr. et al. |
| 6,952,152 B2 | 10/2005 | Miya et al. |
| 6,992,152 B2 | 1/2006 | Lobue et al. |
| 7,411,104 B2 | 8/2008 | Yun et al. |
| 7,498,396 B2 | 3/2009 | Baxter, Jr. et al. |
| 8,791,216 B2 | 7/2014 | Baxter, Jr. |
| 8,816,028 B2 | 8/2014 | Baxter, Jr. |
| 9,040,645 B2 | 5/2015 | Baxter, Jr. |
| 9,637,422 B2 | 5/2017 | Kim et al. |
| 10,202,476 B2 | 2/2019 | Kim et al. |
| 10,640,590 B2 | 5/2020 | Baxter, Jr. |
| 11,124,585 B2 | 9/2021 | Baxter, Jr. |
| 11,174,206 B2 | 11/2021 | Baxter, Jr. |
| 11,214,637 B2 | 1/2022 | Baxter, Jr. |
| 11,214,638 B2 | 1/2022 | Kim et al. |
| 12,116,426 B1 * | 10/2024 | Baxter, Jr. .............. C08F 10/10 |
| 2006/0235252 A1 | 10/2006 | Gartside et al. |
| 2006/0235253 A1 | 10/2006 | Gartside et al. |
| 2012/0238716 A1 | 9/2012 | Baxter, Jr. |
| 2013/0317189 A1 | 11/2013 | Baxter, Jr. |
| 2018/0018808 A1 | 1/2018 | Punjani et al. |
| 2020/0002246 A1 * | 1/2020 | Baxter, Jr. ............. C07C 5/2506 |
| 2020/0199271 A1 | 6/2020 | Baxter, Jr. |

FOREIGN PATENT DOCUMENTS

| | | |
|---|---|---|
| WO | 9526818 A1 | 10/1995 |
| WO | 2000013792 A1 | 3/2000 |
| WO | 2016047445 A1 | 3/2016 |

OTHER PUBLICATIONS

Indian Examination Report dated May 20, 2021 for Application No. 202148004624.

Malaysia Office Action dated Sep. 29, 2021 for Application No. PI2019004684.

International Search Report and Written Opinion for Application No. PCT/2018/018808.

International Search Report and Written Opinion for Application No. PCT/US2019/039869 dated Sep. 9, 2019.

Indian Examination Report dated Mar. 29, 2021 for Application No. 202147003975.

Chemical Market Analytics by OPIS, a Dow Jones Company, "Special Focus: Crude C4 Market Overview", Jul. 20, 2023; 13 pages.

International Search Report and Written Opinion dated Aug. 12, 2024 for Application No. PCT/US24/28930.

Lamprecht et al. 'Hydroisomerization of 1-Pentene to Isopentane In A Single Reactor', Chemical Engineering Communications, May 12, 2009 (May 12, 2009), vol. 196, pp. 1206-1216; p. 1209.

Komatsu et al. 'Dehydroisomerization of butane into isobutene on Pt—Sn intermetallic compounds supported on H-SAPO-11', Journal of Catalysis, Jun. 21, 2006 (Jun. 21, 2006), vol. 241, pp. 426-434; p. 426.

* cited by examiner

345 — Optionally separate the 2-butene from the hydroisomerization product effluent 350 — Optionally isomerize at least a portion of the 2-butene to form an isomerization product effluent comprising isobutylene and normal butylenes (A) 355 — Optionally hydroisomerize the isomerization product effluent (B) 360 — Optionally oligomerize isobutylene present in the isomerization product effluent to form isobutylene oligomers 365 — Optionally crack the isobutylene oligomers to form a third isobutylene-containing feed 370 — Optionally introduce the third isobutylene-containing feed to the polymerization reactor to polymerize isobutylene present in the third isobutylene-containing feed

FIG. 3
(Continued)

PROCESSES FOR CONVERTING C4 FEEDS TO ISOBUTYLENE, POLYISOBUTYLENE, OR DERIVATIVES THEREOF

CROSS-REFERENCE TO RELATED APPLICATIONS

This application is a continuation of U.S. patent application Ser. No. 18/661,249, filed on May 10, 2024, which claims benefit of and priority to U.S. Provisional Patent Application No. 63/577,757, filed on May 19, 2023, U.S. Provisional Patent Application No. 63/629,098, filed on Sep. 20, 2023, and U.S. Provisional Patent Application No. 63/630,397, filed on Jan. 31, 2024, each of which is incorporated herein by reference in its entirety.

FIELD

Embodiments of the present disclosure generally relate to new processes for converting C4 feeds to isobutylene. Embodiments of the present disclosure also generally relate to new processes for converting C4 streams to polyisobutylene ("PIB").

BACKGROUND

Traditional methods of making isobutylene used to make PIB include dehydrogenation of isobutane, back-cracking of isobutylene ethers such as MTBE, dehydration of tert-butyl alcohol produced as a by-product in propylene oxide production, or using the isobutylene present in raffinate-1 petrochemical streams. Collecting isobutylene from raffinate-1 streams is the lowest-cost isobutylene. In the case of making conventional PIB (cPIB), state-of-the-art technologies directly polymerize the isobutylene in the raffinate-1 stream without separation of other butylene isomers also contained in the raffinate-1 stream.

In HR-PIB production, however, state-of-the-art methods require the isobutylene to be of relatively high purity, especially with respect to other isobutylene isomers present in the feed stream to avoid undesirable products. For example, the 1-butene and 2-butene in the feed stream act as chain terminators in the polymerization reaction resulting in polymers with less than the desired amount of the high reactivity vinylidene isomers to be considered HR-PIB. In addition, traditional technologies eliminate 1,3-butadiene from feeds for PIB production as 1,3-butadiene interferes with polymerization. For high-purity isobutylene (HPIB) production, HPIB is traditionally isolated from raffinate-1 streams by an etherification process to produce MTBE and this MTBE is then back-cracked to HPIB. Such state-of-the-art methods, however, produce alcohol impurities and waste. Beyond these challenges, refineries are utilizing raffinate-1 streams in other processes. For example, instead of cracking naphtha (which has been the source of raffinate-1), the advent of cracking abundant cheap ethane to produce ethylene has led to large reductions in the available volume of raffinate-1 and the raffinate-1 contains little or no isobutylene.

There is a need for new processes for forming isobutylene. There is also a need for new processes for forming PIB, such as highly reactive PIB ("HR-PIB).

SUMMARY

Embodiments of the present disclosure generally relate to new processes for converting C4 feeds to isobutylene. Embodiments of the present disclosure also generally relate to new processes for converting C4 feeds to PIB. Also provided is a new source of isobutylene produced from various C4 feeds. Traditional technologies eliminate 1,3-butadiene from feeds for isobutylene and PIB production as 1,3-butadiene interferes with polymerization. In contrast, embodiments described herein enable conversion of crude 1,3-butadiene to isobutylene. To the inventors' knowledge, embodiments of the present disclosure provide the first conversion of crude 1,3-butadiene to isobutylene. Further, embodiments described herein enable the production of PIB from a C4 feed even if the C4 feed does not contain isobutylene.

In an embodiment is provided a process for forming isobutylene, the process comprising. The process includes hydroisomerizing 1,3-butadiene present in a C4 feed to form a hydroisomerization product effluent comprising isobutylene and 2-butene. The process further includes forming an isobutylene feed by separating the isobutylene from the hydroisomerization product effluent.

In another embodiment is provided a process for forming polyisobutylene. The process includes hydroisomerizing a C4 feed comprising 1,3-butadiene in a hydroisomerization reactor to form a hydroisomerization product effluent comprising isobutylene and 2-butene. The process further includes separating the isobutylene from the hydroisomerization product effluent to form a first isobutylene-containing feed. The process further includes forming a reaction mixture comprising a polymerization catalyst and the first isobutylene-containing feed. The process further includes reacting the reaction mixture, in a polymerization reactor, to form a polymerization product effluent comprising polyisobutylene.

In another embodiment is provided a process for forming polyisobutylene. The process includes hydroisomerizing a C4 feed in a hydroisomerization reactor to form a hydroisomerization product effluent comprising isobutylene and 2-butene, and separating the isobutylene from the hydroisomerization product effluent to form a first isobutylene-containing feed. The process further includes forming a reaction mixture comprising a polymerization catalyst and the first isobutylene-containing feed, and reacting the reaction mixture, in a polymerization reactor, to form a polymerization product effluent comprising polyisobutylene. The process further includes separating the polymerization product effluent into a spent polymerization catalyst and a filtrate comprising the polyisobutylene, and removing isobutane and unreacted isobutylene from the filtrate comprising the polyisobutylene to form a C4 separated effluent comprising the polyisobutylene. The process further includes introducing the unreacted isobutylene to the polymerization reactor, removing isobutylene oligomer byproducts from the C4 separated effluent, and cracking the isobutylene oligomer byproducts to form a second isobutylene-containing feed. The process further includes introducing the second isobutylene-containing feed to the polymerization reactor, and separating the 2-butene from the hydroisomerization product effluent. The process further includes isomerizing at least a portion of the 2-butene separated from the hydroisomerization product effluent in an isomerization reactor to form an isomerization product effluent comprising isobutylene and normal butylenes. The process further includes hydroisomerizing the isomerization product effluent in the hydroisomerization reactor.

BRIEF DESCRIPTION OF THE DRAWINGS

So that the manner in which the above recited features of the present disclosure may be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
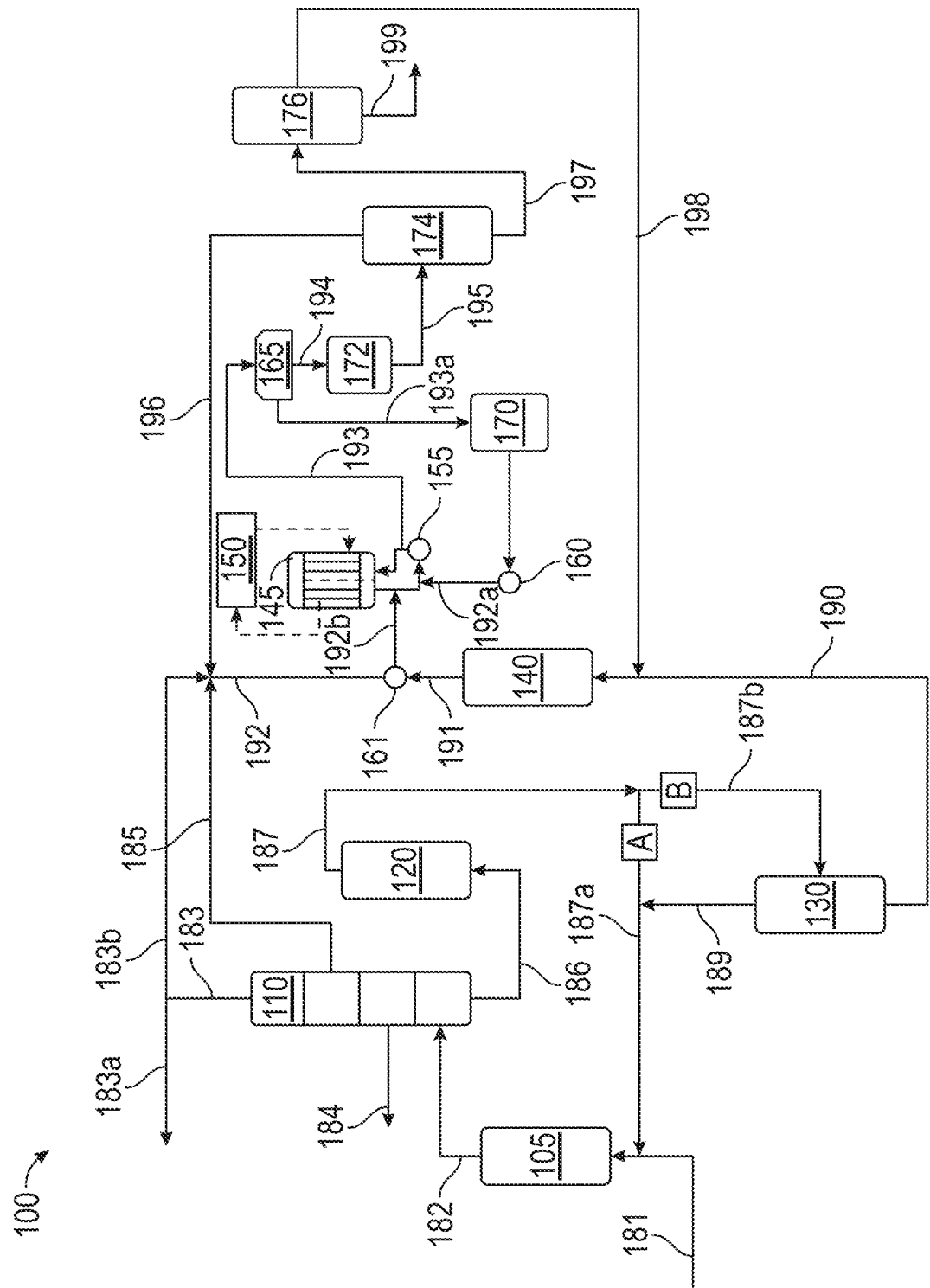
FIG. 1 is a generalized schematic flow diagram showing various embodiments of processes described herein corresponding to operational areas or units in a C4 processing plant.

Embodiments of the present disclosure generally relate to new processes for forming isobutylene. The inventors found a novel processing scheme that converts C4-containing streams (for example, streams that include 1,3-butadiene, 1-butene, 2-butene (cis and/or trans), or combinations thereof) to a product that includes isobutylene. Such processes enable, for example, economically efficient isobutylene production.

Advantageously, the conversion provides a valuable use for low-value normal butylenes and 1,3-butadiene among other C4 streams. For example, instead of flaring the normal butylenes and/or sending streams containing normal butylenes or butadiene to off-site processors, the conversion may advantageously be performed on-site. As used herein, the term "normal butylenes" includes 1-butene and 2-butene(s) (for example, cis-2-butene and/or trans-2-butene). The term "butadiene" and "1,3-butadiene" is used interchangeably herein.

Embodiments of the present disclosure also generally relate to new processes for forming polyisobutylene ("PIB") and highly reactive polyisobutylene ("HR-PIB"). The inventors found a novel processing scheme that advantageously converts all, or nearly all, isobutylene to PIB, for example, HR-PIB. The conversion of isobutylene to PIB, such as HR-PIB, may be integrated with the C4 conversion process to isobutylene such that all or nearly all of the butylenes (for example, normal butylenes and isobutylene) in a feedstock are converted to PIB. The inventors also found a novel processing scheme that converts all, or nearly all, butadiene to PIB, for example, HR-PIB. The conversion of butadiene to PIB, such as HR-PIB, may be integrated with the C4 conversion process to isobutylene such that all or nearly all of the butadiene in a feedstock are converted to PIB. Other C4 streams may be converted to PIB, for example, HR-PIB as described herein.

The use of headings is for purposes of convenience only and does not limit the scope of the present disclosure. Embodiments described herein may be combined with other embodiments.

HR-PIB is a composition that includes greater than about 75% alpha vinylidene olefin isomer. HR-PIB compositions described herein may contain additional olefin isomers including beta vinylidene olefin isomer, other trisubstituted olefin isomers, internal vinylidenes, and tetrasubstituted olefin isomers. As used herein, a "composition" may include component(s) of the composition, reaction product(s) of two or more components of the composition, a remainder balance of remaining starting component(s), or combinations thereof. HR-PIB is termed highly reactive because of its increased reactivity in derivatization reactions, such as reactions with maleic anhydride to produce polyisobutenylsuccinic anhydride (PIBSA) to form precursors useful for fuel and lubricant additives.

cPIB, in contrast to HR-PIB, has a majority of its olefin isomers other than alpha vinylidene. cPIB typically has 10% or less of alpha vinylidene olefin isomer and is therefore significantly less reactive in derivatization reactions than HR-PIB.

The alpha vinylidene olefin isomer (also referred to as α-vinylidene) of a PIB composition (or HR-PIB composition) has the following structure:

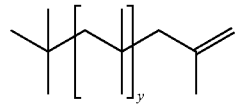

As shown in formula (IA), alpha vinylidene has the double bond (or olefin) positioned in the terminal position of the molecule, allowing it to react more quickly when producing derivatives. As described herein, HR-PIB includes greater than about 75% alpha vinylidene olefin isomer whereas cPIB has about 10% or less of alpha vinylidene olefin isomer.

The beta vinylidene olefin isomer (also referred to as β-vinylidene) of a PIB composition (or HR-PIB composition) has the following structure:

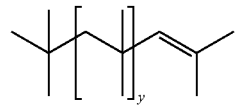

An internal disubstituted vinylidene olefin isomer of a PIB composition (or HR-PIB composition) includes the following structure:

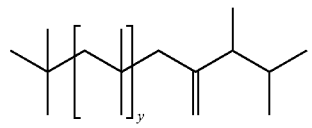

Other internal vinylidenes are possible, including where the position of the olefin in the polyisobutylene is such that the olefin is disubstituted and not at the end of the carbon chain. Other trisubstituted olefin isomers and tetrasubstituted olefin isomers may be produced in the polymerizations described herein.

Traditionally, low molecular weight PIB is made by polymerizing butylenes, particularly isobutylene, contained in industrial butylene streams produced as byproducts in olefin plants. Olefin plants steam crack various hydrocarbon streams including naphtha, gas oils, and more recently lighter hydrocarbons to produce ethylene and propylene. The crude C4 streams (CC4) contain butadiene, isobutylene, normal butylenes (1-butene, 2-butenes (cis and trans isomers)), and butanes. Historically, these CC4 streams are collected and processed in off-site C4 processing facilities to extract the butadiene fraction for use in rubber production.

The resulting substantially butadiene free stream after the butadiene extraction is known as raffinate-1. Raffinate-1 streams contain the residual isobutylene, normal butylenes, and butanes, and such raffinate-1 streams have historically been used as a feedstock for high purity isobutylene production. To produce high purity isobutylene by state-of-the-art methods, the isobutylene in the raffinate-1 stream is removed by reacting it with methanol to make methyl tert-butyl ether ("MTBE"), and the MTBE is back-cracked to produce high purity isobutylene. One of the many drawbacks to this method of producing high purity isobutylene is the alcohol impurities and waste. The stream after removing isobutylene is known as raffinate-2 and contains 1-butene and 2-butenes. 1-Butene and 2-butenes are known as normal butylenes. Because normal butylenes have little economic value, refiners send the raffinate-2 streams to off-site processors or flare the normal butylenes.

An advantage of the present disclosure includes the ability to convert C4 streams (for example, CC4) to high purity isobutylene. Another advantage of the disclosure is the conversion of various C4 streams to PIB such as HR-PIB. That is, the so-called "low value" C4 streams may be upgraded to valuable products such as isobutylene and HR-PIB, among other products.

Traditionally, PIB production is generally carried out in continuous stirred tank reactors (CSTR) normally operating at sub-ambient temperatures using $AlCl_3$ catalysts. Because other butylenes, in addition to isobutylene, are contained in the feed streams, the PIB produced contains significant amounts, typically up to 25%, of normal butylene moieties in the polymer chain. Technically, these polymers are not polyisobutylene but are more correctly polybutylenes (PB).

Many existing methods for PIB production are commonly referred to as Cosden processes. Cosden processes using raffinate-1 streams as feedstocks give very low yields of PIB based on the total stream amount. This is because raffinate-1 streams can contain 20% or lower isobutylene with the balance being normal butylenes and butanes. Normal butylenes have lower reactivity in the polymerization reactions compared to isobutylene, and the butanes do not react. Therefore, yields of PIB based on the total amount of raffinate-1 may be 50% or lower. Even isobutylene extraction techniques—such as MTBE back cracking—to give pure isobutylene for the feed, only yield the isobutylene that was already contained in the raffinate-1 stream. The normal butylenes are not utilized.

PIB, however, has low reactivity due to very low amounts of double bonds (olefins) located at terminal positions and next to the terminal position in the PIB polymer chain. These double bond configurations are known as alpha vinylidene olefin isomers and beta vinylidene olefin isomers respectively, with the alpha vinylidene configuration preferred.

As described above, PIB having large amounts of alpha vinylidene olefin content are termed HR-PIB because the reactivity in the derivative reactions, particularly to make fuel and lubricant additives is greatly enhanced. State-of-the-art HR-PIB production uses liquid $BF_3$ catalyst complexes. These liquid $BF_3$ catalyst complexes are unstable, breaking down into non-reactive species at normal operating temperatures and pressures and are made in situ from $BF_3$ gas and the corresponding alcohol and/or ether on-site at the polymerization facility. $BF_3$ gas is highly toxic and represents a substantial risk to operational personnel and thus requires a significant capital investment to meet all safety and environmental requirements. Liquid catalysts, such as the liquid $BF_3$ catalyst complexes, however, must be quenched post reaction by water washing. Water washing is very difficult, requiring many additional downstream operations, including a series of large mixer/settler units generating copious amounts of waste water containing fluorides that must be disposed. Liquid catalyst removal, therefore, is a significant bottleneck and represents a substantial capital and operational expense in traditional HR-PIB production. Existing HR-PIB processes also require long residence times to effect the polymerization reaction. Residence times, also referred to as reaction times, in these HR-PIB processes are on the order of 30-60 minutes and longer. This means that, for a given capacity, relatively large and extensive reactor units are required with a corresponding increase in capital costs.

Typical HR-PIB production plants must utilize isobutylene feeds that do not contain normal butylenes, and as such, cannot use raffinate-1 type feeds directly. However, high purity isobutylene can be extracted from the raffinate-1 streams by integration with a high purity isobutylene generating unit in the HR-PIB plant. This high purity isobutylene generating unit can extract isobutylene from crude C4 streams by selectively reacting the contained isobutylene with an alcohol to produce a tert-butyl ether, which is then separated from the non-reactive butylenes and butanes and cracked back to a relatively pure isobutylene with regeneration of the alcohol. The back cracking of MTBE is an example of such a process. Another typical method includes extracting isobutylene from CC4 and raffinate streams by back cracking tert-butyl glycol di-ethers to substantially pure isobutylene. The use of glycol, like the MTBE process, remains inefficient. In yet another typical method, the 1-butene in a CC4 or raffinate stream is isomerized to 2-butene and the isobutylene then separated from the higher boiling 2-butene by distillation. In each case, only the isobutylene contained in the CC4 streams is reacted. The normal butylenes do not react and are not utilized. Some of these CC4 streams contain very low levels of isobutylene with normal butylenes as the major contained olefin. Therefore, large amounts of normal butylenes are not utilized.

In contrast to state-of-the-art technologies, processing schemes described herein enable all or nearly all of the butylenes, e.g., normal butylenes and isobutylene, in a CC4 stream to be converted to substantially pure isobutylene. The production of the substantially pure isobutylene may then be integrated with an HR-PIB unit for the production of HR-PIB. The conversion of the butylenes to substantially pure isobutylene may be about 100%. The conversion of isobutylene to HR-PIB may be about 100% with a selectivity to HR-PIB of about 100%.

In contrast to the unstable liquid $BF_3$ catalyst complexes utilized by existing methods, production of HR-PIB as described herein may utilize a solid dispersible catalyst and/or fast reactor technology (for example, a tubular loop reactor). Advantageously, the processes described herein are more cost-efficient than existing processes. Further, processes described herein can be retrofitted to existing PIB plants that use Cosden processes. In addition, these existing PIB plants, may also be retrofitted to use solid dispersible $BF_3$ complex catalysts employing fast-reactor technology with all of the attended benefits and with the further benefit of converting the Cosden PIB product to an HR-PIB product. Existing HR-PIB plants using raffinate streams and other crude streams may also be retrofitted to use processes described herein.

Owing to the lower value of CC4 streams, isobutylene produced from these streams by novel schemes described herein advantageously provides a very cost effective source of isobutylene, especially when integrated with a PIB unit or an HR-PIB unit.

State-of-the-art technologies for forming HR-PIB require isobutylene streams that do not contain normal butylenes. Such streams include high purity isobutylene containing 99+ % isobutylene, isobutylene concentrate (IBC) containing 85-95% isobutylene with the balance being isobutane, dehydro effluent (DHE) containing 45-50% isobutylene with the balance being isobutane, and/or combinations of these streams with the corresponding intermediate isobutylene concentrations. However, such streams are not available in many parts of the world, thereby limiting the areas in which HR-PIB processes can be operated and limiting the commercial usefulness of the HR-PIB processes worldwide. In these and other areas, only crude CC4 and raffinate streams are available, and as discussed above, these streams contain low concentrations of isobutylene with the normal butylenes and/or 1,3-butadiene being the major components. The reaction of normal butylenes in the traditional HR-PIB process reduces the alpha vinylidene olefin isomer content such that the PIB produced is not true HR-PIB. Even if the state-of-the-art processes could be operated such that the normal butylenes do not react, the yield of HR-PIB based on the total feed stream is low. The current disclosure solves, at least, this problem.

Processes described herein may be used to convert an amount of C4 olefins that are not isobutylene (butadiene, 1-butene, cis-2-butene, trans-2-butene, or combinations thereof) in a C4 feed to isobutylene. The conversion of C4 olefins that are not isobutylene to isobutylene by processes described herein may be about 70% or more, about 80% or more, about 90% or more, about 95% or more, about 96% or more, about 97% or more, about 98% or more, about 99% or more, or about 100% based on a total amount of C4 olefins that are not isobutylene in the C4 feed used for the conversion to isobutylene. The total amount of C4 olefins that are not isobutylene in the C4 feed used for the conversion to isobutylene is based on the total amount of butadiene, 1-butene, cis-2-butene, trans-2-butene, or combinations thereof in the C4 feed used for forming isobutylene. The conversion of C4 olefins that are not isobutylene to isobutylene may be such that all, or essentially all, of the C4 olefins that are not isobutylene in the C4 feed are converted to isobutylene. That is, processes described herein may be used to make high purity isobutylene.

Processes described herein may be used to convert an amount of C4 olefins (isobutylene, butadiene, 1-butene, cis-2-butene, trans-2-butene, or combinations thereof) in a C4 feed to HR-PIB. The conversion of C4 olefins to PIB (for example, HR-PIB) by processes described herein may be about 70% or more, about 80% or more, about 90% or more, about 95% or more, about 96% or more, about 97% or more, about 98% or more, about 99% or more, or about 100% based on a total amount of C4 olefins in the C4 feed used for the conversion to HR-PIB. The total amount of C4 olefins in the C4 feed used for the conversion to PIB (e.g., HR-PIB) is based on the total amount of isobutylene, butadiene, 1-butene, cis-2-butene, trans-2-butene, or combinations thereof in the C4 feed for forming the PIB (e.g., HR-PIB). The conversion of C4 olefins to isobutylene may be such that all, or essentially all, of the C4 olefins in the C4 feed are converted to PIB (e.g., HR-PIB). That is, processes described herein may be used for efficient and cost-effective production of PIB (e.g., HR-PIB).

Isobutylene production units described herein may be integrated with PIB production units (for example, HR-PIB production units) described herein, such that the isobutylene output from the isobutylene production unit is used as the C4 feed for the HR-PIB production unit. For example, one or more operations of process 200 may be integrated with one or more operations of process 300. As a non-limiting example, and as described herein, an isobutylene fraction collected from separation unit 110 may be used as a feed for an HR-PIB production unit (e.g., PIB unit 145). Additionally, or alternatively, an isobutylene fraction collected from separation unit 110 may be used in different processes (for example, off-site processes) such as processes for forming rubber, plastics, resins, or other high-value chemicals. As another example, isobutylene oligomer byproducts produced during HR-PIB production (e.g., at PIB unit 145) may be converted to isobutylene by cracking (for example, at cracking unit 140), thereby generating more isobutylene. This isobutylene may be collected for use as a feed for HR-PIB production, may be collected and used in processes for forming other high-value chemicals, or combinations thereof. A non-limiting result of processes described herein is that all, or nearly all, C4 olefins in a C4 feed can be converted with 100%, or near 100%, selectivity to isobutylene and/or a PIB such as HR-PIB.

Further, processing schemes described herein may be integrated with plants that produce CC4 streams such as fluidized catalytic crackers (FCC), steam crackers, or combinations thereof, among others.

Any suitable feed that includes materials containing four carbon atoms (C4) may be utilized such as a C4 hydrocarbon. Any suitable C4 feed that includes a C4 olefin may be utilized. A C4 hydrocarbon may include a C4 olefin, a C4 alkane, or combinations thereof. A C4 olefin is a hydrocarbon containing 4 carbon atoms and at least one double bond (olefin). C4 olefins may include butadiene, normal butylenes (also referred to as n-butylenes), isobutylene, or combinations thereof. C4 alkanes may include butane, such as normal butane (also referred to as n-butane), isobutane (also referred to as i-butane and 2-methylpropoane), or combinations thereof.

The C4 feed useful for embodiments described herein includes 1,3-butadiene as the C4 olefin present in the C4 feed. An amount of 1,3-butadiene in the C4 feed is greater than 3 wt %, such as about 5 wt % or more, about 10 wt % or more, about 30 wt % or more, about 50 wt % or more, about 75 wt % or more, about 80 wt % or more, about 90 wt % or more, about 95 wt % or more, about 99 wt % or more, or about 100 wt % based on the total wt % of the C4 feed. A total amount of 1,3-butadiene in the C4 feed may be greater than 3 wt % to about 99.9 wt % or less, such as from about 5 wt % to about 95 wt %, such as from about 10 wt % to about 90 wt %, such as from about 15 wt % to about 85 wt %, such as from about 20 wt % to about 80 wt %, such as from about 25 wt % to about 75 wt %, such as from about 30 wt % to about 70 wt %, such as from about 35 wt % to about 65 wt %, such as from about 40 wt % to about 60 wt %, such as from about 45 wt % to about 55 wt % based on the total wt % of the C4 feed.

The C4 feed may include at least one C4 olefin in addition to 1,3-butadiene such as, for example, isobutylene, one or more normal butylenes, or combinations thereof. The C4 feed may be a mixed C4 feed, such as a C4 feed that includes one or more C4 olefins and a C4 alkane. The C4 feed may include other materials such as other hydrocarbons, such as a C2 hydrocarbon (ethane), a C3 hydrocarbon (propane), a C5-C40 hydrocarbon, or combinations thereof, including isomers.

The C4 feed may include: 1,3-butadiene; isobutylene; a normal butylene (e.g., one or more of 1-butene, cis-2-butene, trans-2-butene, or combinations thereof); or combinations thereof. The C4 feed may optionally include a butane (e.g., one or more of normal butane (also referred to as n-butane), isobutane (also referred to as i-butane and 2-methylpropoane), or combinations thereof.

The C4 feed may include an effluent obtained from the cracking of hydrocarbons such as naphtha, gas oils, lighter hydrocarbons, or combinations thereof. The C4 feed may include, for example, a crude C4 (CC4) stream comprising 1,3-butadiene and optionally one or more C4 olefins different from 1,3-butadiene. Isobutylene and/or PIB derived from CC4 streams, and other "low value" feeds, as enabled by processes described herein represent a source of low cost isobutylene, particularly for the use in the manufacture of PIB.

A total wt % of a C4 feed used for processes described herein does not exceed 100 wt %. When using any suitable C4 feed, any unreacted portion of the C4 feed may be recycled by or through various parts of processing schemes described herein.

The C4 feed may include a crude C4 (CC4) stream or effluent produced from a steam cracker used to make light hydrocarbon olefins. A steam cracker feed to the steam cracker may include butanes, hexanes, naphtha, or combinations thereof. A steam cracker feed to the steam cracker may include ethane. The CC4 stream or effluent produced from the steam cracker may include 1,3-butadiene, isobutylene, a normal butylene (1-butene, cis-2-butene, and/or trans-2-butene), or combinations thereof. A CC4 stream produced from the steam cracker may include about 3 wt % or more butadiene, about 30 wt % or more butadiene, about 50 wt % or more butadiene based on a total wt % of the CC4 stream.

The C4 feed may include a crude C4 (CC4) stream or effluent produced from a fluidized catalytic cracker (FCC) used to make light hydrocarbon olefins. A FCC feed to the FCC may include butanes, hexanes, naphtha, or combinations thereof. A FCC feed to the FCC may include ethane. The CC4 stream or effluent produced from the FCC may include 1,3-butadiene, isobutylene, a normal butylene (1-butene, cis-2-butene, and/or trans-2-butene), or combinations thereof. A CC4 stream produced from the FCC may include about 3 wt % or more butadiene, about 30 wt % or more butadiene, about 50 wt % or more butadiene based on a total wt % of the CC4 stream, the total wt % of the CC4 stream not to exceed 100 wt %.

The C4 feed may include 1,3-butadiene as the only C4 olefin present in the C4 feed. For example, crude butadiene streams or pure butadiene streams may be utilized as a C4 feed. Existing technologies cannot convert crude (or pure) butadiene streams. Existing technologies convert butylenes present in raff-1 streams (containing less than 3 wt % butadiene) to isobutylene. However, any contained butadiene therein is inert in such existing conversion processes. In contrast, processes of the present disclosure enable the conversion of crude (or pure) butadiene streams to isobutylene.

The C4 feed may include any suitable amount of normal butylenes (1-butene, cis-2-butene, trans-2-butene, or combinations thereof). A total amount of normal butylenes in the C4 feed may be greater than 0.1 wt %, such as from about 1 wt % to 97 wt %, such as from about 5 wt % to about 95 wt %, such as from about 10 wt % to about 90 wt %, such as from about 15 wt % to about 85 wt %, such as from about 20 wt % to about 80 wt %, such as from about 25 wt % to about 75 wt %, such as from about 30 wt % to about 70 wt %, such as from about 35 wt % to about 65 wt %, such as from about 40 wt % to about 60 wt %, such as from about 45 wt % to about 55 wt %, based on the total wt % of the C4 feed.

The C4 feed may include any suitable amount of isobutylene. An amount of isobutylene in a C4 feed may be about 0.01 wt % or less, about 0.05 wt % or less, about 0.1 wt % or less, about 0.5 wt % or less, or about 1 wt % or less based on the total wt % of the C4 feed. Alternatively, an amount of isobutylene in a C4 feed may be greater than 0.1 wt %, such as from about 1 wt % to 97 wt %, such as from about 5 wt % to about 95 wt %, such as from about 10 wt % to about 90 wt %, such as from about 15 wt % to about 85 wt %, such as from about 20 wt % to about 80 wt %, such as from about 25 wt % to about 75 wt %, such as from about 30 wt % to about 70 wt %, such as from about 35 wt % to about 65 wt %, such as from about 40 wt % to about 60 wt %, such as from about 45 wt % to about 55 wt %, or from about 10 wt % to about 45 wt %, such as from about 15 wt % to about 40 wt %, such as from about 20 wt % to about 35 wt %, such as from about 25 wt % to about 30 wt %, based on the total wt % of the C4 feed. Alternatively, an amount of isobutylene in the C4 feed may be about 5 wt % or less, such as from about 0 wt % to about 4 wt %, such as from about 0.1 wt % to about 2 wt %, such as from about 0.5 wt % to about 1 wt %.

Any suitable C4 feed, such as those described herein, may be used for processes for forming isobutylene, for processes for forming PIB, such as HR-PIB, or combinations thereof. In contrast to traditional methods for forming isobutylene and PIB, embodiments described herein enable conversion of 1,3-butadiene to isobutylene and to PIB.

Although embodiments of the present disclosure may be described with respect to forming HR-PIB, embodiments described herein may be used for forming PIB unless specified to the contrary or the context clearly indicates otherwise.

FIG. 1 is a generalized schematic flow diagram showing various embodiments of processes described herein corresponding to operational areas or units in a C4 processing plant 100 according to an embodiment. The C4 processing plant 100 includes embodiments for isobutylene production and PIB (for example, HR-PIB) production. The C4 processing plant 100 may be run in a continuous process.

The C4 feed enters the C4 processing plant 100 through line 181 and is hydroisomerized in hydroisomerization unit 105. The hydroisomerization unit 105 may be a selective hydrogenation unit (SHU). The hydroisomerization unit 105 may include a hydroisomerization reactor. The hydroisomerization converts the C4 feed to a hydroisomerization product effluent that includes isobutylene and 2-butene (cis- and/or trans-2-butene). As described above, the C4 feed may be free of isobutylene as may be the case if the C4 feed came from steam crackers using ethane feed or if the C4 feed is substantially butadiene.

The hydroisomerization in hydroisomerization unit 105 is performed under any suitable conditions effective to convert the C4 feed to a hydroisomerization product effluent that includes isobutylene and 2-butene. It may be beneficial to use the catalyst in at least one downflow fixed catalyst bed reactor. When the proportion of 1,3-butadiene in the cut is high, as is the case, for example, for steam cracking CC4 cut wherein the 1,3-butadiene is not to be extracted, it may be advantageous to effect the transformation in two reactors in series to better control the hydrogenation selectivity. The second reactor may be an upflow reactor and may act as a finisher. The quantity of hydrogen utilized for the reactions carried out in this step may be adjusted as a function of the composition of the cut so that, there is only a slight excess of hydrogen with respect to the theoretical stoichiometry. The operating conditions may be selected so that the reactants and products are liquid. It may, however, be advantageous to select an operating mode such that the products are partially vaporized at the reactor outlet, to facilitate thermal control of the reaction. The temperature for the hydroisomerization in hydroisomerization unit 105 may be from about 20° C. to about 200° C., such as from about 50° C. to about 150° C., such as from about 60° C. to about 150° C. The pressure may be from about 50 pounds per square inch gauge (psig) to about 600 psig, such as from about 50 psig to about 500 psig, such as from about 50 psig to about 400 psig, so that the reactants may be at least partially in the liquid phase. The space velocity may be from about 0.5 $h^{-1}$ to about 10 $h^{-1}$, such as from about 1 $h^{-1}$ to about 6 $h^{-1}$. The catalyst may include a palladium (Pd) metal adsorbed on a substrate, the substrate being a metal oxide such as gamma alumina, at a concentration of about 0.1 wt % to about 10 wt %, such as from about 0.5 wt % to about 5 wt %, such as from about 1.0 wt % to about 2 wt %. Additionally the Pd catalyst may be sulfurized to further improve selectivity and reduce the possibility of over-hydrogenation.

The hydroisomerization product effluent exits the hydroisomerization unit 105 through line 182 and is flowed to a separation unit 110 where components of the hydroisomerization product effluent are separated. For example, the hydroisomerization product effluent may be separated into an isobutylene fraction (which exits separation unit 110 through line 185) and a 2-butene fraction (which exits separation unit 110 through line 186). The hydroisomerization product effluent may also include n-butane, isobutane, or combinations thereof. In such instances the separation unit 110 may also separate an isobutane fraction (which exits separation unit 110 through line 183) and an n-butane fraction (which exits separation unit 110 through line 184). The separation unit 110 may be any suitable apparatus such as a fractional distillation column that separates the components (or fractions) by boiling points.

The separation at separation unit 110 is performed under any suitable conditions effective to separate the various components of the hydroisomerization product effluent. For example, separation unit 110 may include a fractionation column or columns. The fractionation column(s) may be operated with a residence time that is from about 20 minutes to about 100 minutes, such as from about 25 minutes to about 75 minutes, such as from about 30-60 minutes at a column pressure that is from about 50 to about 150 psig, such as from about 50 psig to about 100 psig, such as from about 50 psig to about 75 psig such that the C4 fractions may be condensed with cooling tower water. The fractionation column(s) reboiler may be operated such that isobutane is taken overhead at about 10° F. (about −12° C.) to about 12° F. (about −11° C.) at reflux to provide isobutane at greater than about 90% purity, isobutylene at greater than about 99% purity as a top side draw at about 19° F. (about −7.2° C.) to about 21° F. (about −6.1° C.), n-butane as a bottom side draw at about 29° F. (about −1.7° C.) to about 31° F. (about −0.6° C.), and 2-butene as a bottom stream leaving the fractionation column(s) at greater than 31° F. (about 1.1° C.).

The n-butane fraction exiting the separation unit 110 through line 184 may be collected in storage tanks or flowed into a pipeline where the n-butane fraction may be utilized in other chemical operations or burned as fuel. The isobutane fraction may serve as a solvent makeup for a PIB unit feed (also referred to as a PIB reactor feed). Here, the isobutane fraction exiting the separation unit through line 183 may be flowed through line 183b and combined with a PIB reactor feed in line 192. Pump 161 controls flow of the PIB reactor feed from line 192 into line 192b and into the PIB unit 145. Additionally, or alternatively, the isobutane fraction may be fed to, for example, a refinery alkylation unit (not shown) that converts isobutane into alkylate, a high octane gasoline component. Here, the isobutane fraction exiting the separation unit through line 183 may be flowed through line 183a to the refinery alkylation unit.

The isobutylene fraction exiting the separation unit 110 through line 185 may be combined with a PIB reactor feed in line 192b. The 2-butene exiting the separation unit 110 through line 186 may be introduced into an isomerization unit 120. The isomerization unit 120 may be operated to perform a skeletal isomerization process, SKIP, and in such instances, the isomerization unit 120 may include a SKIP unit. At the isomerization unit 120, at least a portion of the 2-butene (cis-2-butene and/or trans-2-butene) may be isomerized to form an isomerization product effluent, or mixture, that is enriched in isobutylene.

As used herein, an effluent that is "enriched" in, for example, isobutylene, refers to an effluent where the relative amount (or concentration) of isobutylene in an effluent after a process operation (for example, after a skeletal isomerization process) is greater than the relative amount (or concentration) of isobutylene in the effluent before the process operation. For example, if an effluent includes 0.1 wt % isobutylene before a skeletal isomerization process, the effluent formed after the skeletal isomerization process would include greater than 0.1 wt % isobutylene.

Besides 2-butene, the feed for the isomerization operation may include 1-butene and/or isobutylene. At high temperatures and in the presence of a catalyst, the normal butylenes (1-butene and 2-butene) and isobutylene can reach a chemical equilibrium such that the amount of isobutylene can be maximized. The isomerization product effluent exiting the isomerization unit 120 by line 187 may optionally include normal butylenes.

The isomerization at the isomerization unit 120 is performed under any suitable conditions effective to isomerize at least a portion of the 2-butene to an isomerization product effluent having a higher concentration of isobutylene than the concentration of isobutylene in the feed to the isomerization unit 120. That is, the 2-butene feed entering the isomerization unit 120 through line 186 has a lower concentration of isobutylene than the concentration of isobutylene in the isomerization product effluent exiting the isomerization unit 120 by line 187.

The isomerization may be performed by the following non-limiting procedure. A stream of 2-butene (cis-and/or trans-2-butene), optionally 1-butene, and optionally minor amounts of isobutylene is passed over a reactor bed containing a zeolite catalyst, such as a borated beta-zeolite. The isomerization conditions may include a temperature from about 450° C. to about 500° C., a pressure of about atmospheric pressure, and a LHSV from about 4 $h^{-1}$ to about 5 $h^{-1}$, such that the reaction is in the vapor phase. The butylenes vapors may be diluted with nitrogen at a weight ratio from about 1.4 to about 1.5. Selectivity to isobutylene may be greater than about 50%.

The isomerization product effluent exiting the isomerization unit 120 through line 187 may be flowed via path (A), path (B), or combinations thereof. With respect to path (A), the isomerization product effluent exiting the isomerization unit 120 through line 187 may return to the hydroisomerization unit 105 through line 187a. With respect to path (B), the isomerization product effluent exiting the isomerization unit 120 through line 187 may enter line 187b and be introduced into an oligomerization unit 130 (or oligomerization reactor). In FIG. 1, path (A) and path (B) are represented as a "boxed A" and a "boxed B", respectively.

With reference to path (A), the isomerization product effluent flowing through line 187a may be introduced directly to the hydroisomerization unit 105 (not shown). Additionally, or alternatively, the isomerization product effluent flowing through line 187a may be combined with the C4 feed that enters the C4 processing plant 100 through line 181. This combined isomerization product effluent and C4 feed may then be introduced to the hydroisomerization unit 105.

With reference to path (B), the isomerization product effluent that enters the oligomerization unit 130 through line 187b includes isobutylene and optionally a normal butylene (for example, 1-butene, a 2-butene, or combinations thereof). The oligomerization unit 130 may include an oligomerization zone and a separation zone. At the oligomerization zone of the oligomerization unit 130, the isobutylene in the isomerization product effluent is oligomerized to an oligomerization product comprising one or more isobutylene oligomers. The one or more isobutylene oligomers may include isobutylene oligomers having 20 carbon atoms or less (C20 or less), such as dimers, trimers, tetramers, pentamers, or combinations thereof, such as diisobutylene, triisobutylene, tetraisobutylene, pentaisobutylene, or combinations thereof). The oligomerization product may optionally include additional components such as other hydrocarbons, normal butylenes, or combinations thereof.

At the separation zone of the oligomerization unit 130, unreacted normal butylenes present in the oligomerization product, if any, are separated from the isobutylene oligomers. These unreacted normal butylenes separated from the isobutylene oligomers are part of the isomerization product effluent that enters the oligomerization unit 130 by line 187b. Optionally, the isomerization product effluent flowing through line 187b may be separated into an isobutylene fraction and a normal butylenes fraction prior to the oligomerization of isobutylene and the isobutylene fraction flowed to the oligomerization unit 130. Optionally, the oligomerization may be selective for converting isobutylene to the one or more isobutylene oligomers, while the normal butylenes (for example, 1-butene, cis-2-butene, and trans-2-butene) do not react or do not substantially react.

The oligomerization in the oligomerization zone of the oligomerization unit 130 is performed under any suitable conditions effective to oligomerize at least a portion of the isobutylene present in the isomerization product effluent entering the oligomerization unit via line 187b. Suitable catalysts for the oligomerization may include acid catalysts, such as a solid acid catalyst, such as an acidic ion exchange resin compound, for example Amberlyst sulfonic acid resins. As an example, the oligomerization may be performed by the following non-limiting procedure. A process stream comprising isobutylene, which may also contain butanes and other butylene isomers, may be passed through a fixed bed of acidic ion exchange resin, such as Amberlyst 15, at a temperature that may be from about 50° C. to about 150° C. and at an liquid hourly space velocity (LHSV) that may be from about 1 $h^{-1}$ to about 5 $h^{-1}$.

The oligomerization converts at least a portion of isobutylene in the isomerization product effluent that enters the oligomerization unit 130 to the oligomerization product. The percent (%) conversion may be about 50% or more, from about 75% to about 100%, such as from about 85% to about 95%, or greater than about 90%, such as about 91%, such as about 92%, such as about 93%, such as about 94%, such as about 95%, such as about 96%, such as about 97%, such as about 98%, such as about 99%, such as about 100% based on an amount of isobutylene in the isomerization product effluent entering the oligomerization unit 130 through line 187b.

The separation in the separation zone of the oligomerization unit 130 is performed under any suitable conditions effective to separate unreacted normal butylenes from the isobutylene oligomers. Such separation conditions may include maintaining a temperature in the separation zone that is from about 50° C. C to about 150° C. and a LHSV that may be from about 1 $h^{-1}$ to about 5 $h^{-1}$.

The normal butylenes may exit the oligomerization unit 130 (for example, leaving "overhead") through line 189 where the normal butylenes may then be combined with the isomerization product effluent flowing through line 187a. This combined stream of normal butylenes and isomerization product effluent may then be introduced to the hydroisomerization unit 105. Additionally, or alternatively, the normal butylenes flowing through line 189 may be introduced directly to the hydroisomerization unit 105. Additionally, or alternatively, the normal butylenes flowing through line 189 may be combined with the C4 feed flowing through line 181, and the combined normal butylenes and C4 feed may then be introduced to the hydroisomerization unit 105. Additionally, or alternatively, the normal butylenes flowing through line 189 may be combined with the isomerization product effluent flowing through line 187a and with the C4 feed flowing through line 181. This combined stream of normal butylenes, isomerization product effluent, and C4 feed may then be introduced to the hydroisomerization unit 105.

The oligomerization product effluent ("bottoms") comprising the isobutylene oligomers may exit the oligomerization unit 130 through line 190. The oligomerization product effluent comprising the isobutylene oligomers flowing through line 190 may be introduced to a cracking unit 140 (or cracking reactor). The cracking unit 140 breaks down, or cracks, the isobutylene oligomers into a cracking product effluent comprising isobutylene. The cracking product effluent may include a high purity isobutylene, for example, a HR-PIB grade isobutylene.

The cracking of the isobutylene oligomers in the cracking unit 140 is performed under any suitable conditions effective to crack at least a portion of the isobutylene oligomers present in the oligomerization product effluent. Suitable catalysts for the cracking operation may include metal oxides, such as gamma-alumina; activated metal oxides, such as solid $BF_3$ metal oxide complexes; zeolites, such as Y-zeolites; activated zeolites; or combinations thereof. As an example, the cracking may be performed by the following non-limiting procedure. A process stream containing isobutylene oligomers, such as dimers, trimers, tetramers, pentamers, or combinations thereof, may be passed over a magnesium silicate catalyst contained in a suitable fixed bed reactor. The cracking reactor conditions may include a temperature that may be from 250° C. to about 450° C., a pressure that may be about atmospheric pressure, and a LHSV that may be from about 1 h$^{-1}$ to about 5 h$^{-1}$. The process stream containing isobutylene oligomers may be diluted with an inert gas such as nitrogen to a volume percent of from about 10 vol % to about 90 vol %.

The cracking converts at least a portion of isobutylene oligomers in the oligomerization product effluent that enters the cracking unit 140 to the cracking product effluent. The % conversion may be about 50% or more, from about 75% to about 100%, such as from about 85% to about 95%, or greater than about 90%, such as about 91%, such as about 92%, such as about 93%, such as about 94%, such as about 95%, such as about 96%, such as about 97%, such as about 98%, such as about 99%, such as about 100% based on an amount of isobutylene oligomers entering the cracking unit 140 through line 190.

The cracking product effluent exiting the cracking unit 140 via line 191 may then be introduced to the PIB unit 145 (or PIB reactor). The PIB reactor feed in line 192 may be combined with the cracking product effluent so as to enter line 192b, or it may enter the PIB unit 145 separately from the PIB reactor feed. The PIB reactor feed and the cracking product effluent may both contain isobutylene.

The PIB reactor feed, with or without the cracking product effluent, enters the PIB unit 145 via line 192b. In the PIB unit 145, a reaction mixture is formed that includes a polymerization catalyst, and one or more isobutylene-containing feeds. These one or more isobutylene-containing feeds may include the isobutylene fraction that exits separation unit 110 and travels through line 185, line 192, and 192b; the cracking product effluent that flows through line 191; an isobutylene recycle that exits a C4 separation unit 174 and travels through line 196 and 192 (described below); or combinations thereof. Upon reaction a polymerization product effluent comprising a polymer composition is formed. The polymer composition may be or include PIB, such as HR-PIB.

The polymerization in PIB unit 145 is performed under conditions effective to form a polymerization product effluent comprising the polymer composition. Suitable polymerization catalysts and polymerization conditions may include those described in U.S. Pat. Nos. 10,640,590, 11,124,585, 11,214,637, and 11,174,206, each of which is incorporated in its entirety.

As an illustrative, but non-limiting, example, the one or more isobutylene-containing feeds flow into the PIB unit 145 (for example, a PIB reactor or an HR-PIB reactor) in which the reaction mixture may be recirculated in a tubular loop reactor at high linear velocities utilizing an in-line circulation pump 155. A polymerization catalyst may be injected into the reaction mixture via line 192a flowing from a catalyst preparation unit 170 with the assistance of a catalyst feed pump 160. The polymerization reaction is exothermic and takes place in the liquid phase in the reactor tubes at a pressure that may be greater than the autogenous pressure at the given reactor temperature, which may be in the range of about 100 psig to about 150 psig. The reaction temperature may be controlled by coolant flow on a shell side of the reactor supplied by external chilling unit 150. The polymerization product effluent exiting the PIB unit 145 via line 193 includes HR-PIB. The polymerization product effluent may be a crude reaction mixture comprising HR-PIB and one or more optional components. The one or more optional components of the polymerization product effluent may include unreacted isobutylene, isobutane diluent, catalyst residues, or combinations thereof. The one or more optional components may be recycled to various units in the C4 processing plant 100.

Suitable polymerization catalysts include a catalyst system that includes $BF_3$ on a support material. The concentration of $BF_3$ may be greater than about 25 wt %, such as greater than about 30 wt %, such as greater than about 40 wt %, such as greater than about 45 wt %, such as greater than about 50 wt % based on a total weight of the catalyst system. The support material may comprise $Al_2O_3$, $ZrO_2$, $TiO_2$, $SnO_2$, $CeO_2$, $SiO_2$, $SiO_2/Al_2O_3$, or combinations thereof. The support material may be selected from the group consisting of $Al_2O_3$, $ZrO_2$, $TiO_2$, $SnO_2$, $CeO_2$, $SiO_2$, $SiO_2/Al_2O_3$, and combinations thereof. The support material may have a $SiO_2$ content greater than about 45 wt % based on a total weight of the support material. The support material may have an $Al_2O_3$ content between about 25 wt % and about 75 wt %, such as between about 25 wt % and about 50 wt % based on a total weight of the support material.

Additionally, or alternatively, the support material may include an ion exchange resin. Suitable ion exchange resins may include an anionic exchange resin, a cationic exchange resin, an acidic cation exchange resin, a basic anionic exchange resin, or a combination thereof The catalyst system may optionally include a complexing agent. Complexing agents may include methanol (MeOH), ethanol, isopropanol, n-propanol, neopentyl alcohol, dimethyl ether, diethyl ether, diisopropyl ether, diisobutyl ether, di-tert-butyl ether, methyl tert-butyl ether, ethylene glycol, 2,2-dimethylbutanol, 2,2-dimethylpentanol, 2,2-dimethylhexanol, or benzyl alcohol. The complexing agent may be an alcohol that lacks a beta hydrogen such as ethanol, 2,2-dimethyl alcohols (for example, neopentyl alcohol, 2,2-dimethylbutanol, 2,2-dimethylpentanol, and 2,2-dimethylhexanol), benzyl alcohol, and ring-substituted benzyl alcohols. An alcohol with a beta hydrogen may undergo an undesired dehydration/beta-elimination reactions.

When the catalyst system includes a complexing agent, a mole ratio of the complexing agent to $BF_3$ may be between about 0.1 and about 10 in the catalyst complex, such as between about 0.2 and about 5, such as between about 0.2 and 2, such as between about 0.5 and about 2, such as between about 1.0 and about 1.9, such as between about 1.0 and about 1.3, for example, about 1.0, or from about 1.3 to about 1.5, such as about 1.4.

The catalyst system may be a solid, such as powders. The catalyst system may be fed to the PIB unit 145 as a catalyst system feed comprising the catalyst system in a slurry. Here, the catalyst system may be slurried with one or more oligomer byproducts and/or light polymers from PIB polymerization itself (for example, C8-C20 oligomers, such as C12-C20 oligomers, or C8-C16 oligomers, or C8-C12 oligomers, such as C8 and/or C12 PIB, or PIB having a molecular weight from about 350 Da to about 500 Da, or combinations thereof), at about 5-15 wt %, such as about 10 wt % catalyst system concentration. Additionally, or alternatively, the catalyst system may be slurried with a nonpolar carrier solvent such as alkanes from octane through hexadecane and higher alkanes.

The polymerization catalyst, e.g., a catalyst system slurry, may then be injected (for example, via line 192a) into the incoming isobutylene-containing feed stream flowing through line 192b and into the circulation pump line at a point where the physical distance between the injection point in the feed line and the point at which the feed enters the reactor of the PIB unit 145 is at a minimum. The injection point for the catalyst system slurry may be on the suction side of the feed pump (for example, in-line circulation pump 155) to provide mixing.

The polymerization in PIB unit 145 may be performed according to the following non-limiting procedure. A catalyst system feed and an isobutylene-containing feed may be flowed into the PIB unit 145 to form a reaction mixture. The reaction mixture may be maintained at a temperature that is from about −35° C. to about 100° C., such as about 0° C. to about 80° C. Using a slurried catalyst system, the reaction may be carried out in the liquid phase at pressures of at least about autogenous pressures, such as from about 100 psig (about 700 kPa) to about 150 psig (about 1000 kPa)). After a suitable period (for example, a residence time of the isobutylene in the reactor), a polymer composition is obtained. For example, the polymerization may be performed for about 30 minutes or less, such as about 10 minutes or less, such as about 4 minutes or less, such as about 2 minutes or less.

Suitable reactors useful for the polymerization in PIB unit 145 may include batch, tubular loop, continuous stirred tank reactor (CSTR), plug flow, fluidized bed, immobilized bed, and fixed bed. More than one reactor may be operated in series or parallel. These reactors may have or may not have internal cooling or heating, and the feeds may or may not be refrigerated.

Times and temperatures may be controlled such that no significant olefin isomerization occurs during polymerization, and such that conversion and molecular weights are in desirable ranges. Reaction temperatures and pressures, and polymer precursor concentrations, can be selected to control for the Mn of the polymer composition. For example, higher temperatures typically provide polymer compositions with lower Mn.

Temperature control in the polymerization reactor of the PIB unit 145 may be achieved by offsetting the heat of polymerization with reactor cooling by using reactor jackets or cooling coils to cool the contents of the reactor, auto refrigeration, pre-chilled feeds, vaporization of liquid medium (diluent, polymer precursors, or solvent) or combinations of all three. In the case of CSTR with ebullient cooling, the boiling mixture may be cooled with a chilled overhead condenser. For non-ebullient cooled CSTR, any suitable type of heat exchanger may be used to chill the reactor jacket using any suitable cooling media. In some embodiments, a fast reactor is used.

A fast reactor is one in which the reactor is the heat exchanger with the reaction taking place in the tubes with cooling on the shell. Any suitable type of cooling media may be used depending mainly on operating temperature range. Adiabatic reactors with pre-chilled feeds may also be used. In some embodiments, the reactor(s) for the polymerization are operated in as much of an isothermal mode as possible. Non-isothermal reactor operation may result in broader molecular weight distributions. In series operation with two or more polymerization reactors, a second reactor temperature may be higher than a first reactor temperature. In parallel reactor operation, the temperatures of the two reactors may be independent.

For CSTR, a concentration of the catalyst system in the reaction mixture for CSTR may be from about 1,000 ppm to about 2,000 ppm based on a total weight of the catalyst system slurry, wherein a $BF_3$ concentration in the catalyst system slurry may be from about 250 ppm to about 500 ppm based on the total weight of the catalyst system slurry. Residence times may be on the order of less than about 600 minutes, such as less than about 120 minutes, such as less than about 60 minutes, or from about 30 minutes to about 60 minutes, and may be controlled by catalyst system concentration. Higher catalyst system concentrations in the catalyst system slurry can increase the reaction rate. The polymerization reaction can be highly exothermic and a limiting factor to reaction rate can be the ability to remove the heat of reaction.

In state-of-the-art plants that utilize CSTR, the reaction mixture comprising the catalyst system can be flowing upward in the reactor, through at least a first portion and a second portion. The first portion of the reactor may be relatively narrow to provide higher velocity and higher catalyst system mixing. The second portion of the reactor may be wider to provide lower velocity and less catalyst system mixing, allowing for some settling of the catalyst system back into the reaction zone. The crude reaction mixture may exit near the top of the reactor with some catalyst system being carried out with the exiting crude reaction mixture. The catalyst system exiting the reactor may be made up with catalyst system from a catalyst system injection such that a constant catalyst system amount is maintained in the reactor. The reaction temperature may be maintained by vaporization of a portion of the isobutylene containing feed controlled by the reactor pressure; higher reactor pressure may give higher reaction temperature according to the vapor pressure curve of the system butylenes. Mn of the polymer may be controlled by reaction temperature with higher reaction temperature giving lower Mn. Reaction temperatures from about −5° C. to about 5° C. may provide polymers having an Mn of about 2,300 Daltons. Reaction temperatures from about 18° C. to about 22° C. may provide polymers having an Mn of about 1,000 Daltons. The crude reaction mixture leaving the reactor may be treated with aqueous caustic streams to quench and wash out the catalyst system.

Alternatively, the plants may be modified to include a catalyst system filtration (or other solid-liquid separation devices as described below) to remove the catalyst system thereby eliminating the water washing operations and the need to dispose of waste water containing catalyst system residues. Optionally, a water washing operation may be performed depending on application or type of plant. Removal of the catalyst system also allows for recycling of the catalyst system. The plants can also include one or more distillation units as described below.

For fast reactor modes, the PIB unit 145 may include tubular loop reactor. Here, the PIB unit includes a tube-in-shell heat exchanger with the polymerization reaction taking place in the tubes and cooling provided through the shell side of the heat exchanger with the heat of the polymerization reaction taken out by an external chiller unit. A reactor design for PIB unit 145 includes a two-pass heat exchanger. Using a slurried catalyst system, the reaction may be carried out in the liquid phase at pressures of at least about autogenous pressures, typically greater than about 0 psig (0 kPa), such as from about 35 psig (about 250 kPa) to about 300 psig (about 2100 kPa), such as from about 100 psig (about 700 kPa) to about 150 psig (about 1000 kPa)).

The PIB unit 145 may be, or include, a tubular loop reactor for the polymerization reaction. In such embodiments, a circulation loop is provided to deliver high velocity in the tubes at a Reynolds number of the circulating liquid in the tubes that may be about 2,000 or more. Reynolds numbers of about 2,000 or more allow for turbulent flow in the tubes which increases the heat exchange and the ability to remove the heat of reaction in very short periods of time. The ability to quickly remove the heat of reaction allows for operation at very short residence times. A residence time in the tubular loop reactor may be less than about 60 minutes, less than about 30 minutes, less than about 10 minutes, less than about 4 minutes, less than about 3 minutes, less than about 2 minutes, or less than about 1 minute; alternately, from about 30 seconds to about 4 minutes. A concentration of the catalyst system in the reaction mixture may be from about 500 ppm to about 10,000 ppm based on a total weight of the catalyst system slurry, and wherein a $BF_3$ concentration in the reaction mixture is from about 125 ppm to about 2,500 ppm based on the total weight of the catalyst system slurry. Alternatively, the concentration of the catalyst system in the reaction mixture may be from about 1,000 ppm to about 5,000 ppm based on a total weight of the catalyst system slurry, and wherein the $BF_3$ concentration in the reaction mixture may be between about 250 ppm to about 1,250 ppm based on the total weight of the catalyst system slurry. Alternatively, the concentration of the catalyst system in the reaction mixture may be greater than about 2,000 ppm based on a total weight of catalyst system slurry, and wherein the $BF_3$ concentration may be greater than about 500 ppm based on the total weight of the catalyst system slurry.

In various embodiments, the polymerization reactor of the PIB unit 145 may include a tubular loop reactor. The tubular loop reactor may employ a circulation loop independent of a feed flow of an isobutylene-containing feed to the polymerization reactor (e.g., the isobutylene containing feed in line 192b) such that a velocity of the reaction mixture in the tubular loop reactor is about 3 ft/sec (about 0.9 m/sec) or more, such as from about 6 ft/sec (about 1.8 m/sec) to about 10 ft/sec (up to about 3.05 m/s). Such velocities enable turbulent flow.

The circulation loop (where the reaction mixture is present) is independent of the feed flow as they are controlled by different pumps. The circulation loop where the reaction mixture is present may be controlled by the in-line circulation pump 155 and the feed flow may be controlled by pump 161. Pump 161 controls flow of the isobutylene containing feed into line 192b and into the PIB unit 145.

A ratio of the circulation flow of the reaction mixture in the circulation loop to the feed flow of the isobutylene containing feed may be about 10:1 or more, such as from about 10:1 to about 50:1. Such a ratio enables turbulent flow.

For tubular loop reactors, the catalyst system may be slurried with one or more oligomer byproducts and/or light polymers from PIB polymerization itself (for example, C8-C20 oligomers, such as C12-C20 oligomers, or C8-C16 oligomers, or C8-C12 oligomers, such as C8 and/or C12 PIB, or PIB having a molecular weight from about 350 Da to about 500 Da, or combinations thereof), at about 5-15 wt %, such as about 10 wt % catalyst system concentration. Additionally, or alternatively, the catalyst system may be slurried with a non-polar carrier solvent such as alkanes from octane through hexadecane and higher alkanes, at about 5-15 wt %, such as about 10 wt % catalyst system concentration. The polymerization catalyst (for example, a catalyst system slurry) may then be injected via line 192a into the incoming isobutylene-containing feed stream flowing through line 192b as described herein.

In at least one embodiment the polymerization occurs in the presence of a solid dispersible $BF_3$ complex catalyst and/or in a high-speed reactor, such as a fast reactor. As an example, the polymerization operation may be performed by the following procedure. High purity isobutylene may be fed to a tubular loop reactor and slurried in situ with a solid catalyst system described herein such that the catalyst concentration is in the range of from about 2,000 ppm to about 1,000 ppm. The residence time in the reactor is less than about 4 minutes. The crude HR-PIB effluent (as an example polymerization product effluent) can then be purified as described below.

The polymerization reaction in PIB unit 145 converts at least a portion of isobutylene in an isobutylene containing feed that enters the PIB unit 145 to a polymerization product effluent comprising PIB (for example, HR-PIB). The % conversion to PIB (or HR-PIB) may be about 50% or more, from about 75% to about 100%, such as from about 85% to about 95%, or greater than about 90%, such as about 91%, such as about 92%, such as about 93%, such as about 94%, such as about 95%, such as about 96%, such as about 97%, such as about 98%, such as about 99%, such as about 100% based on an amount of isobutylene entering the PIB unit 145.

The polymerization process that occurs in PIB unit 145 produces polymer compositions, such as PIB, for example, HR-PIB. The PIB may have a number average molecular weight, Mn, of about 320 Daltons (Da) or more, such as from about 320 Da to about 10,000 Da, such as from about 350 Da to about 5,000 Da, from about 700 Da to about 2,250 Da, or about 350 Da, or about 700 Da, or about 950 Da, or about 1300 Da, or about 2,250 Da.

The polyisobutylene may have a polydispersity index (PDI), which is the ratio of Mw/Mn, of about 5 or less, such as about 2.5 or less, about 2 or less, about 1.5 or less, or about 1.3 or less.

The polymer composition (for example, PIB) may include a first portion comprising polymer chains having alpha vinylidene groups (alpha vinylidene olefin isomers), a second portion comprising polymer chains having beta vinylidene groups (beta vinylidene olefin isomers), and a third portion comprising polymer chains having internal vinylidene groups (internal vinylidene olefin isomers).

The polymer composition may be an HR-PIB, where the first portion may be 75 wt % or more, such as about 80 wt % or more, such as about 82 wt % or more, such as about 85 wt % or more, such as about 87 wt % or more, such as about 90 wt % or more, such as about 92 wt % or more, such as about 94 wt % or more, such as about 95 wt % or more of the polymer composition based on a total wt % of the polymer composition, the total wt % of the polymer composition not to exceed 100 wt %. The second portion plus the third portion may be 25 wt % or less, such as about 20 wt % or less, such as about 18 wt % or less, such as about 15 wt % or less, such as about 13 wt % or less, such as about 10 wt % or less, such as about 8 wt % or less, such as about 6 wt % or less, such as about 5 wt % or less of the polymer composition based on the total wt % of the polymer composition.

Alternatively, the polymer composition may be a mid-range vinylidene PIB. Mid-range vinylidene PIBs have an alpha vinylidene content less than 75%, such as about 65% or less. In these and other embodiments, the mid-range vinylidene PIB may include: a first portion comprising polymer chains having alpha vinylidene groups, a second portion comprising polymer chains having beta vinylidene groups, and a third portion comprising polymer chains having internal vinylidene groups, wherein: the first portion may be less than 75 wt %, such as from greater than 10 wt % to less than 75 wt %, such as from 40 wt % to less than 75 wt % such as from about 50 wt % to about 65 wt % of the polymer composition based on a total wt % of the polymer composition, the total wt % of the polymer composition not to exceed 100 wt %; and the second portion plus the third portion may be from greater than about 25 wt % to about 60 wt % or less, such as from about 35 wt % to about 50 wt % based on the total wt % of the polymer composition.

After the polymerization product effluent leaves (or is discharged from) the PIB unit 145 through line 193, the polymerization product effluent may be purified by separation, atmospheric stripping, vacuum stripping, or a combination thereof to remove byproducts, unreactive compounds, catalyst residues, and unreacted polymer precursors. Unreacted polymer precursors may be recycled. For example, such purification may be accomplished in a plant by passing the crude polymer composition through a solid-liquid separation device and then through a pressure distillation column to remove the unreacted polymer precursors and other non-reacted residues. The distillation columns may be atmospheric and/or vacuum distillation columns. Such embodiments are described below.

Referring back to FIG. 1, the polymerization product effluent exiting the PIB reactor via line 193 may be introduced to a solids separation unit 165 for catalyst removal. Here, the catalyst residues (comprising, e.g., spent polymerization catalyst) may be separated or otherwise removed from the polymerization product effluent. After sufficient separation in the solids separation unit 165, the solids (e.g., catalyst residues) may exit the solids separation unit 165 by line 193*a* and may then be introduced to a catalyst preparation unit 170 through line 193*a*. At the catalyst preparation unit 170, the catalyst residues may be regenerated into an active polymerization catalyst. That is, the catalyst preparation unit 170 may be used to regenerate the polymerization catalyst which may then be recycled back to the PIB unit 145. Additionally, or alternatively, the catalyst preparation unit 170 may be utilized to make fresh, or unused, polymerization catalyst which may then be fed to the PIB unit 145.

The catalyst preparation unit 170 may include a catalyst mix tank with a high shear pump, a boron trifluoride ($BF_3$) complex tank, a solvent tank, and a substrate hopper. The polymerization catalyst may be a solid $BF_3$ complex as described herein. The solid $BF_3$ catalyst is stable with an almost indefinite shelf life when handled properly. As an alternative to on-site preparation in the catalyst preparation unit 170, the polymerization catalyst may be made or obtained off-site and mixed with solvent on-site.

The regenerated polymerization catalyst, the fresh polymerization catalyst, or both may be fed to the PIB unit 145 from the catalyst preparation unit 170 through line 192*a* with the aid of catalyst feed pump 160.

The separation of the solid catalyst (for example, catalyst residues) from the polymerization product effluent in the solids separation unit 165 results in a PIB containing filtrate (also called a solid catalyst-depleted effluent comprising the PIB). The PIB containing filtrate may be an HR-PIB containing filtrate (also called a solid catalyst-depleted effluent comprising the HR-PIB). As used herein, an effluent that is "depleted" in, for example, solid catalyst, refers to an effluent where the relative amount (or concentration) of solid catalyst in an effluent after a process operation (for example, after a solids separation process) is less than the relative amount (or concentration) of solid catalyst in the effluent before the process operation. For example, if an effluent includes 0.1 wt % solid catalyst before a solids separation process, the effluent formed after the solids separation process would include less than 0.1 wt % solid catalyst. The solid catalyst-depleted effluent may include minor amounts of solid catalyst, for example, less than 100 ppm.

The HR-PIB containing filtrate (the solid catalyst-depleted effluent) comprising the HR-PIB may still be crude at this stage, containing byproducts, unreacted materials, and/or impurities. The HR-PIB containing filtrate may exit the solids separation unit 165 through line 194 and then be introduced to one or more units that purify the HR-PIB and strip byproducts, unreacted materials, and/or impurities from the solid catalyst-depleted effluent in order to form a high purity HR-PIB effluent exiting the C4 processing plant 100 via line 199. These one or more units that purify the HR-PIB may include a defluorinating unit 172, a C4 separation unit 174 (or stripping column or distillation column), an oligomer separation unit 176 (for example, a stripping column), or combinations thereof. These one or more units that purify the HR-PIB are optional depending on the purity levels desired for the HR-PIB. For example, the HR-PIB filtrate may be introduced into the defluorinating unit 172 only, or the HR-PIB filtrate may be introduced to the C4 separation unit 174 and the oligomer separation unit 176. That is, the HR-PIB filtrate may bypass one or more of the defluorinating unit 172, C4 separation unit 174, and the oligomer separation unit 176.

The HR-PIB containing filtrate may exit the solids separation unit via line 194 and enter an defluorinating unit 172 that serves to separate or remove fluorine-containing species (e.g., HF, organic fluorides, etc.) from the HR-PIB containing filtrate. The defluorinating unit 172 may be an adsorption polishing unit that includes an alumina adsorption bed that traps, separates, or otherwise removes fluorine-containing species from the HR-PIB containing filtrate. The defluorinating unit 172 may be operated under conditions effective to remove fluorine-containing species from the HR-PIB containing filtrate. Such conditions may include a column temperature that is from about 10° C. to about 50° C., such as from about 10° C. to about 35° C., and most preferably in the range of 25° C. to about 35° C. at a weight hourly space velocity (WHSV) that is from about 1 $h^{-1}$ to about 60 $h^{-1}$ or more.

The defluorinated effluent comprising the HR-PIB may exit the defluorinating unit 172 through line 195. The defluorinated effluent comprising the HR-PIB may optionally include additional components such as isobutane, unreacted isobutylene, isobutylene oligomer byproducts, or combinations thereof. The defluorinated effluent comprising the HR-PIB and optional additional components may then be introduced to the C4 separation unit 174. The C4 separation unit 174 serves to remove or otherwise separate the one or more optional additional components present in the defluorinated effluent from the HR-PIB. The C4 separation unit 174 may include a debutanizer column, debutanizer fractionator, a distillation column, a fractional distillation column, or combinations thereof.

The C4 separation unit 174 may be operated under any suitable conditions effective to remove the one or more optional additional components from the defluorinated effluent. For example, the C4 separation operation in the C4 separation unit 174 may be performed with the following example conditions. The defluorinated effluent may be passed through a distillation column operating at weight hourly space velocity WHSV that may be from about 1 $h^{-1}$ to about 60 $h^{-1}$ (or more), at a column temperature that may be from about 25° C. to about 100° C., and a column pressure that may be from about 25 psi (about 172 kPa) to about 100 psi (about 689 kPa).

Isobutane, unreacted isobutylene, or combinations thereof (if any) may exit the C4 separation unit 174 (e.g., leaving overhead) through line 196 where the isobutane, unreacted isobutylene, or combinations thereof may then be combined with the PIB reactor feed in line 192. This combined stream may then be introduced into the PIB unit 145 via line 192*b*.

Additionally, or alternatively, the isobutane, unreacted isobutylene, or combinations thereof flowing through line 196 may be introduced directly to the PIB unit 145. Additionally, or alternatively, the isobutane, unreacted isobutylene, or combinations thereof flowing through line 196 may be combined with the isobutylene feed flowing through line 185 and the combined feed flowed into the PIB unit 145. Additionally, or alternatively, the isobutane, unreacted isobutylene, or combinations thereof flowing through line 196 may be combined with the isobutane feed flowing through line 183b and the combined feed flowed into the PIB unit 145.

The C4 separated effluent (also referred to as a debutanized effluent) may exit the C4 separation unit 174 through line 197. After the C4 separation in the C4 separation unit 174, an amount of HR-PIB in the C4-separated effluent (or debutanized effluent) may be about 50 wt % or more, about 70 wt % or more, about 85 wt % or more, about 90 wt % or more, about 91 wt % or more, such as about 92 wt % or more, such as about 93 wt % or more, such as about 94 wt % or more, such as about 95 wt % or more, such as about 96 wt % or more, such as about 97 wt % or more, such as about 98 wt % or more, such as about 99 wt % or more, such as about 100 wt % based on a total wt % of the C4 separated effluent exiting the C4 separation unit 174 through line 197.

The C4 separated effluent comprising the HR-PIB flowing through line 197 may optionally include one or more additional components such as isobutylene oligomer byproducts (e.g., C20 or lower isobutylene oligomer byproducts, such as C8-C20 isobutylene oligomer byproducts, such as C12-C16 isobutylene oligomer byproducts), polymerization catalyst solvent (e.g., the component used to form catalyst slurry), or combinations thereof. The C4 separated effluent comprising the HR-PIB and optional additional components may then be introduced to the oligomer separation unit 176. The oligomer separation unit 176 serves to remove or otherwise separate the one or more optional additional components present in the C4 separated effluent from the HR-PIB. The oligomer separation unit 176 may include a distillation column, a fractional distillation column, or combinations thereof.

The oligomer separation unit 176 may be operated under any suitable conditions effective to remove the one or more optional components, e.g., isobutylene oligomers, from the C4 separated effluent. Suitable conditions for operating the oligomer separation unit 176 may include passing the C4 separated effluent through a distillation column operating at a temperature that may be from about 150° C. to about 275° C. and a pressure that may be from about 1 millimeter of mercury (mmHg) to about 100 mmHg, such as from about 10 mmHg to about 50 mmHg.

The isobutylene oligomer byproducts, polymerization catalyst solvent, or combinations thereof (if any) may exit the oligomer separation unit 176 (leaving "overhead") through line 198 where the isobutylene oligomer byproducts, polymerization catalyst solvent, or combinations thereof (if any) may then be combined with the isobutylene oligomers in line 190. This combined stream may then be introduced into the cracking unit 140. Additionally, or alternatively, the isobutylene oligomer byproducts, polymerization catalyst solvent, or combinations thereof (if any) may be introduced directly to the cracking unit 140. Additionally, or alternatively, the isobutylene oligomer byproducts, polymerization catalyst solvent, or combinations thereof (if any) may be introduced to the catalyst preparation unit 170 where it may be used to form a catalyst slurry.

The oligomer separated effluent comprising the HR-PIB ("bottoms" stream) may exit the oligomer separation unit 176 through line 199. The oligomer separated effluent may be a highly pure (e.g., >95% pure, such as about 98% or more, such as about 99% or more, such as 100%) PIB composition or HR-PIB composition based on a total wt % of the oligomer separated effluent.

As described, various fractions, feeds, byproducts, or combinations thereof may be recycled and fed, either directly or indirectly, back through one or more units/operations of the C4 processing plant 100. Product removal and the recycling of various materials may aid in driving the various unit operations closer and closer to completion and may serve to increase the selectivity of the C4 feed to isobutylene to 100% or nearly 100%. In addition, product removal and the recycling of various materials may serve to increase the selectivity of the C4 feed to HR-PIB to 100% or nearly 100%.

It is noted that various units described in the C4 processing plant 100 described herein may contain one or more reactors. For example, hydroisomerization unit 105 may include one or more hydroisomerization reactors (e.g., one or more SHUs) such as two or more hydroisomerization reactors.

Figure 2:
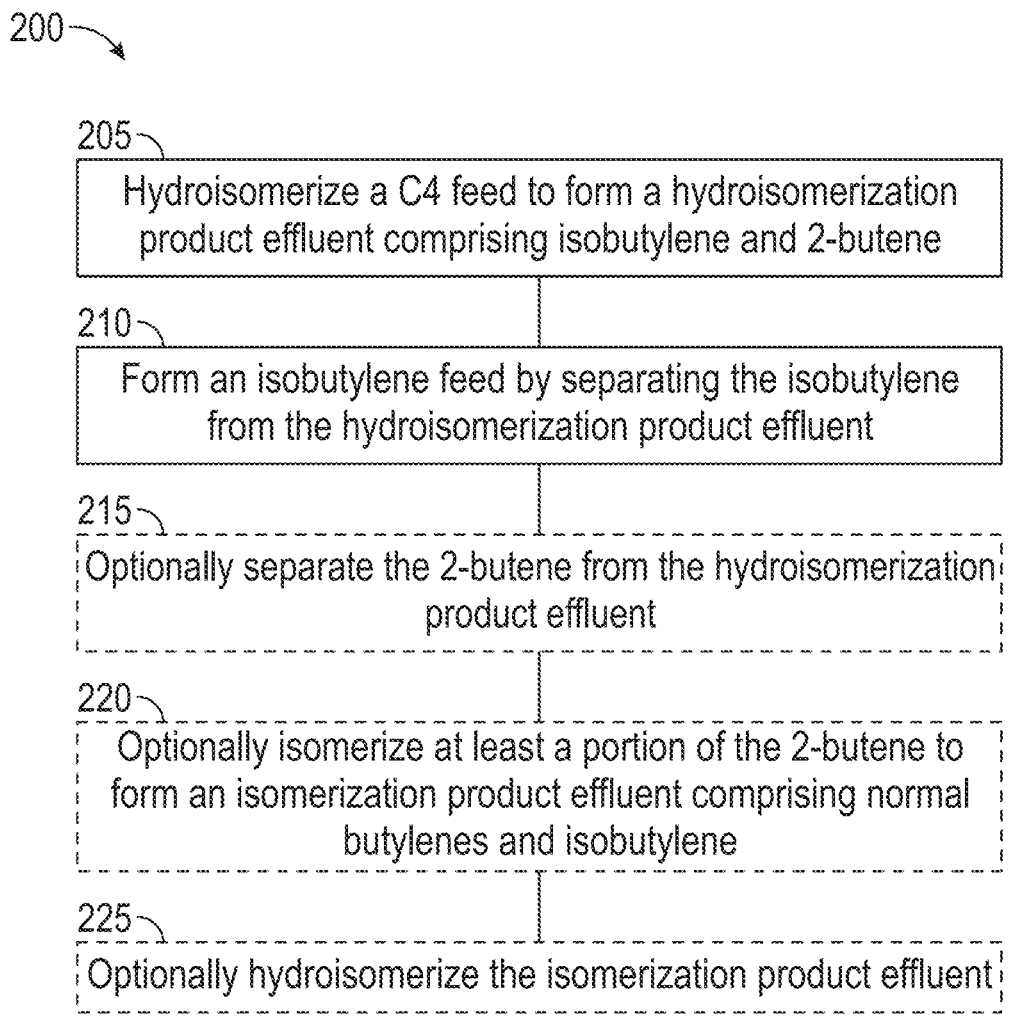
FIG. 2 is a flow diagram showing selected operations of a process for forming isobutylene according to at least one embodiment.

FIG. 2 is a flow diagram showing selected operations of a process 200 for forming isobutylene according to at least one embodiment. The process 200 includes hydroisomerizing a C4 feed to form a hydroisomerization product effluent that includes isobutylene and 2-butene at operation 205. The hydroisomerization process of operation 205 may occur in the hydroisomerization unit 105. Here, for example, a C4 feed is introduced to hydroisomerization unit 105 via line 181 and the hydroisomerization product effluent exits the hydroisomerization unit 105 through line 182. Any suitable C4 feed may be used such as those described above.

Useful C4 feeds include 1,3-butadiene, and to the inventors' knowledge, embodiments of the present disclosure provide the first conversion of crude 1,3-butadiene to isobutylene. In some examples, the C4 feed may include 3 wt % or more, such as 5 wt % or more, of 1,3-butadiene based on a total wt % of the C4 feed, the total wt % of the C4 feed not to exceed 100 wt %.

The process 200 further includes forming an isobutylene feed by separating the isobutylene from the hydroisomerization product effluent at operation 210. The separation process of operation 210 may occur in the separation unit 110. For example, the hydroisomerization product effluent may be introduced to the separation unit 110 and an isobutylene fraction may be separated from the hydroisomerization product effluent, exiting the separation unit 110 by line 185.

The process 200 may optionally include separating the 2-butene (e.g., cis- and/or trans-2-butene) from the hydroisomerization product effluent at optional operation 215. For example, a 2-butene fraction may be separated from the hydroisomerization product effluent utilizing the separation unit 110. The 2-butene fraction may exit the separation unit 110 by line 186. Other fractions such as n-butane, isobutane, or combinations thereof (if any) may optionally be separated from the hydroisomerization product effluent utilizing the separation unit 110.

The process 200 may optionally include isomerizing at least a portion of the 2-butene present in the 2-butene fraction (formed by optional operation 215) at optional operation 220. The isomerization process of optional operation 220 results in an isomerization product effluent comprising normal butylenes and isobutylene. The isomerization process of optional operation 220 may be performed using isomerization unit 120 which may be a SKIP unit. For example, the 2-butene fraction present in line 186 may be introduced into the isomerization unit where at least a portion of the 2-butene (cis-2-butene and/or trans-2-butene) may be isomerized to form an isomerization product effluent, or mixture, that is enriched in isobutylene. The isomerization product effluent may exit the isomerization unit 120 via line 187.

The process 200 may optionally include hydroisomerizing the isomerization product effluent at optional operation 225. The hydroisomerization process of optional operation 225 may be performed in the hydroisomerization unit 105. For example, the isomerization product effluent flowing through line 187*a* may be introduced to the hydroisomerization unit 105 to undergo hydroisomerization.

Additionally, or alternatively, process 200 may include combining the isomerization product effluent with the C4 feed. For example, the isomerization product effluent flowing through line 187*a* may combine with the C4 feed flowing through line 181. The resulting mixture after combining the isomerization product effluent with the C4 feed includes isobutylene and the components of the C4 feed. The resulting mixture optionally includes normal butylenes (e.g., 1-butene, cis-2-butene, and/or trans-2-butene) formed during the isomerization process of optional operation 220. This mixture may then be hydroisomerized in the hydroisomerization unit 105.

The ability to recycle the isomerization product effluent back through one or more operations of process 200 enables more isobutylene to be formed. A net result of the process 200 is the formation of a high purity isobutylene from C4 feeds such as crude C4 feeds.

Figure 3:
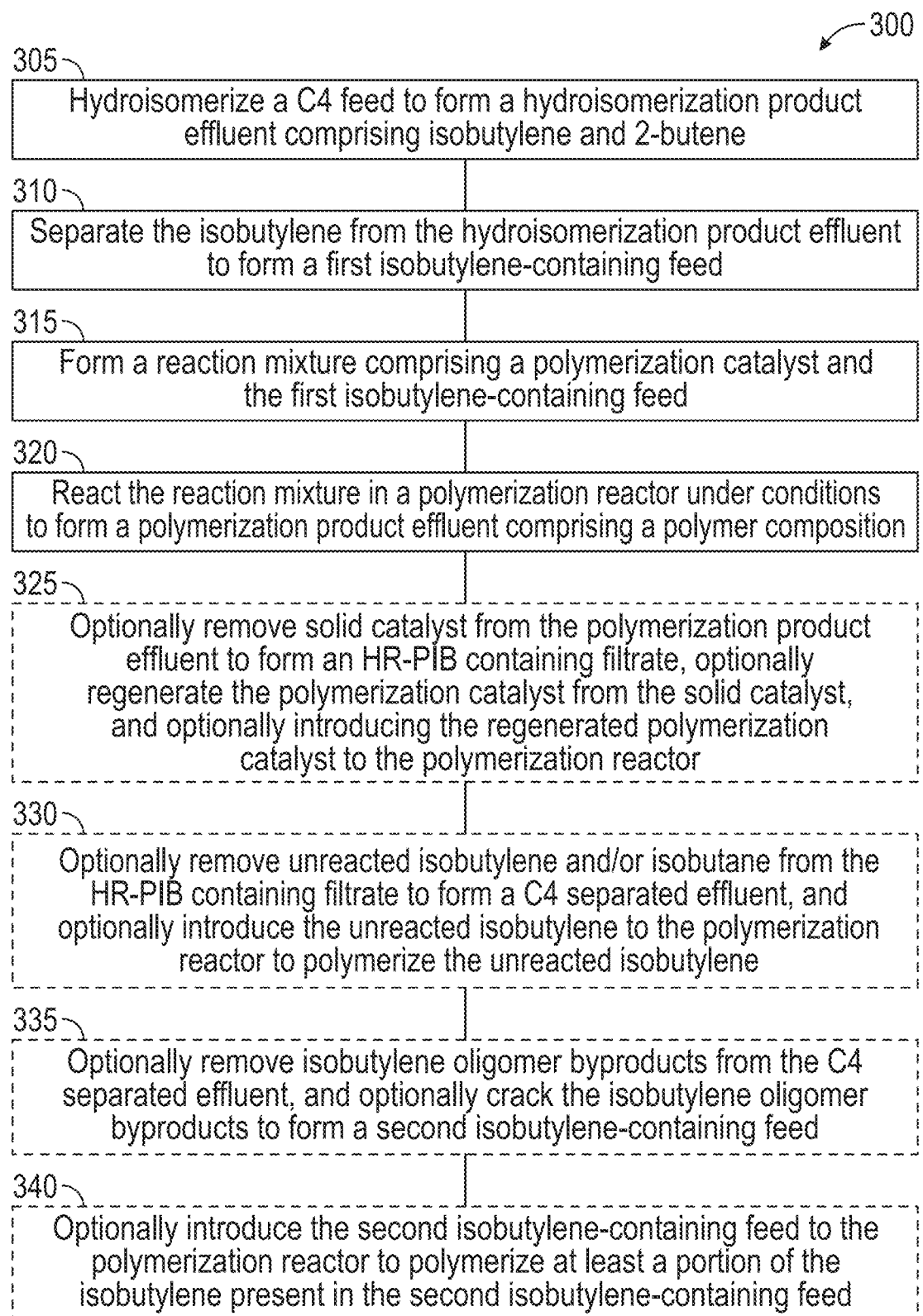
FIG. 3 is a flow diagram showing selected operations of a process for forming PIB (e.g., HR-PIB) according to at least one embodiment.

FIG. 3 is a flow diagram showing selected operations of a process 300 for forming PIB, such as HR-PIB, according to at least one embodiment. Process 300 may include one or more operations shown in FIG. 2, such as operation 205, operation 210, optional operation 215, optional operation 220, or optional operation 225.

The process 300 includes hydroisomerizing a C4 feed to form a hydroisomerization product effluent that includes isobutylene and 2-butene (cis-2-butene and/or trans-2-butene) at operation 305. Operation 305 may be the same as or similar to operation 205 of FIG. 2. The hydroisomerization process of operation 305 may be performed in the hydroisomerization unit 105.

The process 300 further includes separating isobutylene from the hydroisomerization product effluent to form a first isobutylene-containing feed at operation 310. Operation 310 may be the same as or similar to operation 210 of FIG. 2. The separation process of operation 310 may be performed in the separation unit 110. The isobutylene fraction separated from the hydroisomerization product effluent is referred to as the first isobutylene-containing feed. The first isobutylene-containing feed exits the separation unit 110 by line 185.

The process 300 further includes forming a reaction mixture comprising a polymerization catalyst and the first isobutylene-containing feed at operation 315. The reaction mixture formed at operation 315 may be performed in the PIB unit 145 (a polymerization reactor) by combining the first isobutylene-containing feed flowing through line 192*b* with the polymerization catalyst (which may be in the form of a slurry) flowing through line 192*a*. Suitable polymerization catalysts, such as a solid $BF_3$ complex, are described herein. The first isobutylene-containing feed and the polymerization catalyst may be circulated in the PIB unit 145 with the assistance of the in-line circulation pump 155.

The process 300 further includes reacting the reaction mixture in a polymerization reactor (e.g., PIB unit 145) under conditions effective to form a polymerization product effluent comprising a polymer composition at operation 320. Suitable conditions for the reaction (polymerization) process of operation 320 are described herein. For example, the reaction mixture in the polymerization reactor may be maintained at a temperature that is from about −35° C. to about 100° C., such as from about 0° C. to about 80° C. Using a slurried catalyst system, the reaction may be carried out in the liquid phase at pressures of at least about autogenous pressures, such as from about 100 psig (about 700 kPa) to about 150 psig (about 1000 kPa)). After a suitable period (e.g., a residence time of the isobutylene in the reactor), a polymer composition is obtained. The polymerization may be performed for a period of about 30 minutes or less, such as about 10 minutes or less, such as about 4 minutes or less, such as about 2 minutes or less.

The polymer composition of the polymerization product effluent formed at operation 320 includes a PIB, such as HR-PIB.

Prior to the reaction (polymerization) process of operation 320, the first isobutylene-containing feed may be mixed with a C4 olefin-containing stream that is different from the first isobutylene-containing feed. This may be accomplished by adding a line (not shown in FIG. 1) that meets with line 192 and/or line 192*b*. Upon mixing of the first isobutylene-containing feed with the different C4 olefin containing stream, an HR-PIB grade stream having an isobutylene content greater than about 50 wt % may be formed. The different C4 olefin containing stream may be any C4 feed described herein that includes a C4 olefin, such as raffinate-1. The ability to mix and upgrade other C4 streams provides another benefit of processes described herein.

The process 300 may include optional operation 325, which includes: (a) optionally removing solid catalyst (e.g., catalyst residues) from the polymerization product effluent to form a PIB containing filtrate (e.g., HR-PIB containing filtrate) at optional operation 325; (b) optionally regenerating a polymerization catalyst from the solid catalyst; and (c) optionally introducing the regenerated polymerization catalyst to the polymerization reactor. Optional operation 325 enables the recycling and/or reuse of the polymerization catalyst.

Here, the polymerization product effluent may exit the PIB unit 145 via line 193 and then be introduced to the solids separation unit 165 to remove the solid catalyst during operation (a) of optional operation 325. The solid catalyst may be removed by filtration, centrifugation, and/or any other suitable solid-liquid separation process. Unlike existing processes that utilize liquid catalysts, the use of a solid polymerization catalyst as described herein enables efficient and productive removal of the spent solid catalyst, as well as regeneration of the polymerization catalyst.

The separated solid catalyst may exit the solids separation unit 165 via line 193*a* and then be introduced to the catalyst preparation unit 170. At the catalyst preparation unit 170, the separated solid catalyst may be transformed into the polymerization catalyst, such that the polymerization catalyst is regenerated during operation (b) of optional operation 325. Additionally, or alternatively, the separated solid catalyst may be removed from the process and discarded. Following regeneration of the polymerization catalyst in the catalyst preparation unit 170, the regenerated polymerization catalyst may be introduced to the polymerization reactor (e.g., the PIB unit 145) via line 192*a* and with the aid of catalyst feed pump 160. The regenerated polymerization catalyst may be in the form a slurry as described herein. Additionally, or alternatively, fresh polymerization catalyst may be prepared in the catalyst preparation unit 170 and/or prepared off-site. The fresh polymerization catalyst may be fed to the polymerization reactor via line 192a and with the aid of catalyst feed pump 160.

The process may further include optional operation 330, which includes: (a) optionally removing unreacted isobutylene and/or isobutane from the PIB containing filtrate (e.g., HR-PIB containing filtrate) to form a C4 separated effluent; and (b) optionally introducing the unreacted isobutylene to the polymerization reactor to polymerize the unreacted isobutylene. Optional operation 330 enables the recycling and/or reuse of at least a portion of the unreacted isobutylene, at least a portion of the isobutane, or combinations thereof. Optional operation 330 enables the recycling and/or reuse of the unreacted isobutylene and/or isobutane.

During operation (a) of optional operation 330, the PIB containing filtrate (e.g., HR-PIB containing filtrate) (formed at optional operation 325) may exit the solids separation unit 165 via line 194. The PIB containing filtrate (e.g., HR-PIB containing filtrate) flowing through line 194 may then be introduced to the C4 separation unit 174. At the C4 separation unit, the unreacted isobutylene, isobutane, or both are separated or otherwise removed from the PIB containing filtrate (e.g., HR-PIB containing filtrate) to form the C4 separated effluent comprising PIB (e.g., HR-PIB).

During operation (b) of optional operation 330, and as described herein, the unreacted isobutylene, isobutane, or combinations thereof (if any) may exit the C4 separation unit 174 via line 196. The unreacted isobutylene, isobutane, or combinations thereof may then be introduced to the polymerization reactor (e.g., PIB unit 145). At the polymerization reactor, the unreacted isobutylene may be polymerized to PIB, such as HR-PIB.

Although not shown in FIG. 3, the process 300 may further include optionally removing fluorine-containing species from the PIB containing filtrate (e.g., HR-PIB containing filtrate). Removal of the fluorine-containing species may be performed in defluorinating unit 172 and may occur, for example, after optional operation 325 and before optional operation 330.

Process 300 may further include optional operation 335, which includes: (a) optionally removing isobutylene oligomer byproducts from the C4 separated effluent formed in operation (a) of optional operation 330; and (b) optionally cracking the isobutylene oligomer byproducts to form a second isobutylene-containing feed.

Here, the C4 separated effluent exiting the C4 separation unit 174 via line 197 may include isobutylene oligomer byproducts formed during polymerization, such as C20 or lower isobutylene oligomer byproducts, such as C8-C20 isobutylene oligomer byproducts, such as C12-C20 isobutylene oligomer byproducts, such as C12-C16 isobutylene oligomer byproducts. During operation (a) of optional operation 335, the fraction containing isobutylene oligomer byproducts may be removed utilizing oligomer separation unit 176, exiting via line 198. By removing the isobutylene oligomer byproducts, another fraction is collected and includes a high purity PIB, or high purity HR-PIB. The high purity PIB may be collected, thereby exiting the C4 processing plant 100 via line 199. During operation (b) of optional operation 335, the isobutylene oligomer byproducts may then be flowed via line 198 to the cracking unit 140 which cracks the isobutylene oligomer byproducts to the second isobutylene-containing feed.

The process 300 may further include introducing the second isobutylene-containing feed via, for example, line 191 and/or line 192b to the polymerization reactor (e.g., PIB unit 145) to polymerize at least a portion of the isobutylene present in the second isobutylene-containing feed at optional operation 340. The polymerization process of optional operation 340 may be the same as, or similar to, operations 315-320. Overall, the combination of optional operations 335 and 340 enable the recycling and/or reuse of the isobutylene oligomer byproducts formed during the polymerization reaction by cracking them into, e.g., a high-purity isobutylene feed (second isobutylene-containing feed). The resulting isobutylene formed from the cracking serves as a second isobutylene-containing feed that may be polymerized to PIB, such as HR-PIB.

The process 300 may further include optional operation 345 which includes separating the 2-butene (e.g., cis- and/or trans-2-butene) from the hydroisomerization product effluent formed in operation 305. Optional operation 345 may be the same as, or similar to, optional operation 215 of FIG. 2. Optional operation 345 may be performed in separation unit 110.

The process 300 may further include optional operation 350 which includes isomerizing at least a portion of the 2-butene present in the 2-butene fraction (formed at optional operation 345) to an isomerization product effluent comprising isobutylene and optionally normal butylenes. The isomerization process of optional operation 350 may be performed in isomerization unit 120 (e.g., a SKIP unit). Optional operation 350 may be the same as, or similar to, optional operation 220 of FIG. 2. The isomerization process of optional operation 350 results in an isomerization product effluent enriched in isobutylene.

As described above, the isomerization product effluent exiting the isomerization may return to the hydroisomerization unit 105 via line 187a (path (A)) and/or may enter line 187b and be introduced into oligomerization unit 130 (or oligomerization reactor) (path (B)). Accordingly, the process 300 may further include optionally hydroisomerizing the isomerization product effluent, or a portion thereof, at optional operation 355, representing the path (A) embodiment. The hydroisomerization process of optional operation 355 may be the same as, or similar to, optional operation 225 of FIG. 2.

Additionally, or alternatively, the process 300 may further include oligomerizing isobutylene present in the isomerization product effluent, or a portion thereof, to form isobutylene oligomers at optional operation 360, representing the path (B) embodiment. Here, the isomerization product effluent flowing through line 187b may be introduced to the oligomerization unit 130. In the oligomerization zone of the oligomerization unit 130, isobutylene present in the isomerization product effluent may be converted to isobutylene oligomers, such as C20 or lower isobutylene oligomers, such as C8-C20 isobutylene oligomers, such as C12-C20 isobutylene oligomers, such as C12-C16 isobutylene oligomers. In the separation zone of the oligomerization unit 130, unreacted normal butylenes present in the oligomerization product, if any, are separated from the isobutylene oligomers. These unreacted normal butylenes may then be fed to the hydroisomerization unit 105.

The process 300 may further include cracking the isobutylene oligomers (formed in optional operation 360) to form a third isobutylene-containing feed at optional operation 365. Here, the isobutylene oligomers flowing through line 190 may be introduced to the cracking unit 140. At the cracking unit 140, the oligomers are broken down to a cracking product effluent comprising isobutylene (e.g., the third isobutylene-containing feed). The third isobutylene-containing feed may be, or include, a high purity isobutylene, e.g., a HR-PIB grade isobutylene.

The process 300 may further include introducing the third isobutylene-containing feed to the polymerization reactor (e.g., PIB unit 145) to polymerize isobutylene present in the third isobutylene-containing feed at optional operation 370. The polymerization process of optional operation 370 may be the same as, or similar to, operations 315-320 and/or optional operation 340.

Process 300 enables various fractions, feeds, byproducts, or combinations thereof to be recycled and fed, either directly or indirectly, back through one or more units/operations of a C4 processing plant, e.g., C4 processing plant 100. Product removal and the recycling of various materials may aid in driving the various operations closer and closer to completion and may serve to increase the selectivity of the C4 feed to PIB (e.g., HR-PIB) to 100% or nearly 100%. A net result of the process 300 is the formation of a high purity PIB, such as high purity HR-PIB from C4 feeds such as crude C4 feeds.

The following examples are put forth so as to provide those of ordinary skill in the art with a complete disclosure and description of how to make and use aspects of the present disclosure, and are not intended to limit the scope of aspects of the present disclosure. Efforts have been made to ensure accuracy with respect to numbers used (e.g. amounts, dimensions, etc.) but some experimental errors and deviations should be accounted for.

EXAMPLES

Examples of forming isobutylene or polymer compositions (e.g., HR-PIB) was performed by processes of the present disclosure. Here, various C4 feeds were investigated for conversion to isobutylene or for conversion to HR-PIB. The Test Methods describes, e.g., methods of characterizing isobutylene produced by processes described herein as well as polymer compositions produced by processes described herein.

Test Methods

Polymer Compositions. The type and amount of each olefin isomer (e.g., alpha vinylidene, beta vinylidene, and other isomers) was determined by $^{13}$C NMR. $^{13}$C NMR spectra were collected using a 500 MHz Bruker pulsed Fourier transform NMR spectrometer equipped with a 10 mm Broad Band Observation (BBO) probe at about room temperature. The polymer sample was dissolved in chloroform-d ($CDCl_3$) and transferred into a 10 mm glass NMR tube. Typical acquisition parameters were inverse-gated (IG) decoupling, a 90° pulse, and a 40 second relaxation delay. Chemical shifts were determined relative to the $CDCl_3$ signal which is set to about 77.2 ppm. To achieve maximum signal-to-noise for quantitative analysis, multiple data files may be added together. The spectral width was adjusted to include all of the NMR resonances of interest. $^{13}$C NMR chemical shifts ($CDCl_3$) for the olefin carbon atoms are provided below in Table A. All data provided in Table A is approximate values. In Table A, the chemical shift provided corresponds to the carbon underlined.

TABLE A $^{13}$C NMR Chemical Shifts of Polymer Compositions

| Type of Olefin Isomer | Chemical Shifts, ppm |
|---|---|
| alpha vinylidene isomer | 143 (R_C_($CH_3$)=$CH_2$); |
|  | 115 (RC($CH_3$)=_C_$H_2$) |
| beta vinylidene isomer | 136 (R_C_(H)=C($CH_3$)$_2$); |
|  | 128 (RC(H)=_C_($CH_3$)$_2$) |
| terminal trisubstituted vinylidene isomer (1) | 134 (R_C_($CH_3$)=CH($CH_3$)); |
|  | 123 (RC($CH_3$)=_C_H($CH_3$)) |
| terminal trisubstituted vinylidene isomer (2) | 139 (R_C_(H)=C($CH_3$)($CH_2CH_3$)); |
|  | 130 (RC(H)=_C_($CH_3$)($CH_2CH_3$) |
| terminal tetrasubstituted vinylidene isomer | 133 (R_C_($CH_3$)=C($CH_3$)$_2$); |
|  | 122 (RC($CH_3$)=_C_($CH_3$)$_2$) |
| internal disubstituted vinylidene isomer | 149 (R_C_(=$CH_2$)($CH_3$)); |
|  | 111 (RC(=_C_$H_2$)($CH_3$)) |

When the alpha vinylidene isomer content (wt %) was determined to be about 75 wt % or greater, the polymer composition comprises HR-PIB. When the alpha vinylidene isomer content (wt %) was determined to be less than 75 wt %, the polymer composition comprises a mid-range vinylidene PIB. Generally, HR-PIB has the following content: alpha vinylidene content (≥75 wt % or more); beta vinylidene isomer (<10-15 wt %); terminal trisubstituted vinylidene isomer (1) (<1 wt %); terminal trisubstituted vinylidene isomer (2) (<2-5 wt %); terminal tetrasubstituted vinylidene isomer (<2-5 wt %); internal disubstituted vinylidene isomer (<2-5 wt %).

Polymer molecular weight. Molecular weights (weight-average molecular weight, Mw, number-average molecular weight, Mn), and PDI (ratio of Mw/Mn) were determined using gel permeation chromatography (GPC). Equipment included a Waters Alliance 2695 HPLC system with a differential refractive index detector (DRI). A typical GPC procedure was to dissolve the sample to be tested in tetrahydrofuran (THF) at a concentration of about 1 wt % to about 10 wt %. The polymer solution was pumped through a series of columns packed with Styragel beads of known porosity. Typical pore diameters range from about 10,000 Å down to about 50-100 Å, and a typical column string includes a $10^4$ Å column, a $10^3$ Å column, a 1000 Å column and a 2-100 Å column. For example, Waters Styragel HR columns 1, 3, and 4 may be used. The nominal flow rate was about 1.0 ml/min. The various transfer lines, columns, and differential refractometer (the DRI detector) were contained in an oven maintained at about 40° C. Elution solvent was THF. There was a 105-sample carousel for automatic injections. Empower 2 was the software system for controlling the separation and analysis.

The columns were calibrated with known molecular weight standards, both narrow distribution standards and broad distribution standards (for example, polystyrene standards from a molecular weight of 500 to 400K). From the calibration, Mn and Mw were determined for a polymer sample. PDI is the ratio of Mw/Mn.

Polymer solutions for GPC were prepared by placing the dry polymer in a glass container, adding the desired amount of THF, and then filtering the mixture through a 0.45-micron nylon or polytetrafluoroethylene (PTFE) filter. All quantities were measured gravimetrically. The concentration of polymer to THF was about 10 mg/ml to 20 mg/ml.

Prior to running each sample, the DRI detector and the injector were purged. Flow rate in the apparatus was then increased to about 0.5 ml/minute, and the DRI was allowed to stabilize for about 8 hours to about 9 hours before injecting the first sample. Each sample run takes about one hour to complete.

Percent yield of isobutylene from crude C4. First, the total butylenes (isobutylene, 1,3-butadiene, 1-butene, and 2-butene (cis and trans)) content of the CC4 stream was determined by GC analysis as described below. The percent yield of isobutylene was determined gravimetrically by dividing the total weight of isobutylene recovered by the total weight of the butylenes in the CC4 stream and multiplying by 100.

Isobutylene conversion to PIB and percent yield. Isobutylene conversion to HR-PIB was determined by gas chromatography according to ASTM D424-09 on an Agilent 6890 Gas Chromatograph with dual flame ionization detector using a 30 meter Restek RTX column and Zero grade nitrogen carrier gas at a flow rate of about 30 cc/min with a split ratio of 10. Percent yield of HR-PIB was determined gravimetrically by dividing the weight of the HR-PIB product recovered by the weight of the isobutylene used in the polymerization and multiplying by 100. Selectivity was determined gravimetrically by dividing the weight of the HR-PIB product recovered by the sum of the oligomers and HR-PIB produced and multiplying by 100.

Example 1

Process for Forming HR-PIB Using Steam Cracker Effluent

For this example, an effluent from a steam cracker (ethane cracker) was separated to obtain a crude C4 (CC4) feed that was used as the C4 feed for forming HR-PIB. The CC4 content of the steam cracker effluent was about 8 wt % to about 10 wt % based on the total wt % of the steam cracker effluent. Table 1A shows the composition of the CC4 effluent from the steam cracker and therefore the composition of the CC4 feed used for forming HR-PIB. In Table 1A, total butylenes refers to the total amount of isobutylene and normal butylenes (1-butene, cis-2-butene, and trans-2-butene) in the CC4 feed, and total butanes refers to the total amount of normal butane and isobutane in the CC4 feed.

TABLE 1A

Typical CC4 Feed Composition

| Components of CC4 Feed | Wt % of the CC4 Feed |
|---|---|
| Butadiene | 39.5 |
| Isobutylene | 28.0 |
| 1-butene | 16.6 |
| 2-butenes (cis and trans) | 11.0 |
| Iso- and normal-butanes | 4.8 |
| Total | 99.9 |

1A. Example Process for Forming HR-PIB (Ex. 1-1)

The CC4 feed was subjected to example processes of the present disclosure for forming HR-PIB. Selected parameters for the process for forming HR-PIB included the following: The CC4 feed was continuously pumped into a hydroisomerization reactor (a fixed bed reactor fixed with sulfurized palladium on alumina catalyst such as a SHU) in an up-flow direction at a rate of 1,000 grams/hour and a pressure of 150 psig. Hydrogen (mixed with methane) was also injected into the reactor at a rate of 17.0 grams/hour. The temperature was 55° C. at the inlet and rises to about 100° C. at the reactor outlet. The effluent was then flowed into a second hydroisomerization reactor (a fixed bed reactor such as a SHU) with the same catalyst operating in a downflow direction essentially isothermally at 75° C. and 150 psig pressure to finish the reaction. The SHU was operated initially for 1 hour to ensure steady state operation. The SHU was then operated for an additional 1 hour and the effluent collected. After the excess hydrogen and methane were removed, gas chromatography analysis showed the composition of the collected SHU effluent to be 27.6 parts by weight (pbw) iso- and normal-butanes, 18.2 pbw isobutylene, 0 pbw 1-butene, 54.2 pbw (cis and trans)-2-butene, and 0 pbw 1,3-butadiene, indicating that all 1-butene and 1,3-butadiene had been converted to 2-butene. The total weight of the collected SHU effluent was 993 grams.

A fractionation column was operated such that the iso-and normal-butylenes were separated and rejected from the process, and the isobutylene was separated and collected. The 2-butene bottom stream from the fractionation column, comprising >90 pbw 2-butene, was continuously fed to a fixed bed isomerization reactor fixed with the proton form of a borated zeolite catalyst operated at a WHSV of 1.5 h$^{-1}$ at an isothermal temperature of 450° C. The conversion of 2-butene was about 49% with a selectivity to isobutylene of 73% to give an isobutylene yield of 36% per pass. The effluent from the isomerization reactor was recycled to the hydroisomerization reactor. The overall yield of isobutylene separated and collected from the fractionation column based on the total of the C4 olefins (1,3-butadiene, 1-butene, and (cis/trans)-2-butene) contained in the steam cracker crude C4 stream was 100%.

The isobutylene fraction collected from the fractionation column was pumped into an HR-PIB fast reactor at a rate of 100 grams/minute with a circulation rate of 3,276 cc/min at a WHSV of 30 h$^{-1}$ and a temperature of 22° F. (−5.6° C.) and pressure of 150 psig. Solid BF$_3$ MeOH complex with mole ratio of MeOH to BF$_3$ of 1.4 was co-fed with the isobutylene feed at a rate of 0.33 cc/min. The reactor was operated for 2 hours until isothermal reaction temperature had been established. The reactor was then operated for an additional 2 hours during which time the reactor effluent was collected in a stirred flask containing 1,000 cc of 10% aqueous NH4OH to quench the catalyst. After 5 hours, the isobutylene feed was stopped and the collection flask was heated to 50° C. to allow the unreacted isobutylene to vent off. When the unreacted isobutylene vent was complete as evidenced by no further weight loss, the contents of the flask were transferred to a separatory funnel and the aqueous layer containing the neutralized catalyst residues was separated from the upper organic layer containing the crude HR-PIB product. The organic layer was washed with deionized (DI) water (3×250 ml portions). The weight of the organic layer was 376 grams indicating an isobutylene conversion of 75.2 wt %. For purposes of calculation, the isobutylene is assumed to be recycled to the HR-PIB reactor feed to give 100% conversion based on the total amount of isobutylene feed.

A 100 gram sample of the crude debutanized HR-PIB was transferred to a 250 ml round bottom vacuum flask. The flask containing the crude debutanized HR-PIB was attached to a rotary evaporator, slowly heated to 225° C. at a pressure of 15 mmHg, and held for two hours to remove the isobutylene oligomeric byproducts. After being allowed to cool, the weight of the final water white HR-PIB product was 93.7 grams, indicating an isobutylene selectivity to HR-PIB of 93.7%. GPC analysis showed the molecular weight to be 2,308 Daltons with a polydispersity (Mn/Mw) of 2.6. The alpha vinylidene isomer content was 83.1 wt % by NMR analysis. The 6.3 grams of oligomeric byproducts were quantitatively converted to isobutylene by heating at 300 degrees Celsius over gamma-alumina in a tube furnace under a stream of N$_2$ for two hours. Conversion of the oligomers to isobutylene and subsequently to HR-PIB gave an HR-PIB yield based on the total weight of the CC4 feed stream of 75.9% and 100% yield based on the butylene olefin isomers contained in the CC4 feed.

1B. Comparative Example Process for Forming HR-PIB (C.Ex. 1-1)

A comparative example process for forming HR-PIB from the CC4 feed was performed. The comparative example is taken from U.S. Pat. No. 6,207,115, Example 1. The comparative example process was performed under the same temperature, pressure, and time conditions as the example process of Ex. 1-1. Table 1B shows the results for the conversion of the feed to HR-PIB by the example process and the comparative process.

TABLE 1B

Percent (%) Yield of HR-PIB and % Conversion of C4 Olefins to HR-PIB

| Example | % Yield of HR-PIB based on total CC4 content of steam cracker effluent | % Conversion of C4 olefins in CC4 Feed to HR-PIB |
|---|---|---|
| Ex. 1-1 | 75.9 | 100 |
| C. Ex. 1-1 | 28.0 | 29.4 |

Overall, the data in Table 1B indicated that processes of the present disclosure are significantly improved over state-of-the-art processes. For example, example process (Ex. 1-1) converts all of the butadiene and all of the total butylenes to HR-PIB, providing a yield of 75.9% based on the total CC4 content of the feed. The butanes (24.1 wt % of the feed) are inert, and therefore 100% conversion of the C4 olefins present in the CC4 feed was observed for Ex. 1-1. In contrast, the comparative example process (C.Ex. 1-1), representing state-of-the-art technologies, provided a very poor yield of 14.0%, leaving a very large amount of unreacted butylenes and butadiene. This example shows that embodiments described herein significantly outperform state-of-the-art technologies for the conversion of crude CC4 effluent streams from a steam cracker to HR-PIB.

Example 2

Process for Forming HR-PIB Using Butadiene

For this example, the C4 feed for forming HR-PIB was >99% butadiene. The butadiene (>99%) was subjected to example processes of the present disclosure for forming HR-PIB as described in Example 1-1. There is no existing method for converting >99% butadiene to HR-PIB.

TABLE 2

% Yield of HR-PIB and % Conversion of C4 Olefins to HR-PIB

| Example | % Yield of HR-PIB based on total CC4 content of butadiene feed | % Conversion of C4 olefins in butadiene feed to HR-PIB |
|---|---|---|
| Ex. 2-1 | >99 | 100 |

Overall, the data in Table 2 indicated that processes of the present disclosure are significantly improved over state-of-the-art processes. For example, example process (Ex. 2-1) converts all of the butadiene to HR-PIB, providing a yield of >99% based on the total CC4 content of the feed. Based on the butadiene alone, 100% conversion of the C4 olefins present in the butadiene feed was observed for Ex. 2-1. As described above, there is no existing method for converting >99% butadiene to HR-PIB. Overall, this example shows that embodiments described herein may be utilized for the conversion of butadiene to HR-PIB.

Example 3

Example Process for Forming Isobutylene: Conversion of Crude C4 from Naphtha Steam Cracker to Isobutylene There is no existing method for converting CC4 from a naphtha steam cracker to isobutylene. Instead, some state-of-the-art technologies include hydroisomerization of 1,3-butadiene to 2-butene but no isomerization of 2-butene to isobutylene. Other state-of-the-art technologies include conversion of all butylenes in a raffinate-1 stream to isobutylene, but no butadiene is contained in the raffinate-1 stream. Other state-of-the-art technologies include isomerizing 1-butene to 2-butene to aid in isobutylene separation but no isomerization step to generate more isobutylene.

For this example of the present disclosure, an effluent from a steam cracker (naphtha steam cracker) was separated to obtain a crude C4 (CC4) feed that was used as the C4 feed for forming isobutylene. Table 3 shows the composition of the CC4 feed used for forming isobutylene in this example.

TABLE 3

Typical CC4 Feed Composition

| Components of CC4 Feed | Parts by weight (pbw) of the CC4 Feed |
|---|---|
| iso- and normal butanes | 4.8 |
| isobutylene | 28.0 |
| 1-butene | 16.6 |
| 2-butenes (cis and trans) | 11.0 |
| 1,3-butadiene | 39.5 |
| Total | 99.9 |

The CC4 feed was continuously introduced to a hydroisomerization reactor (a fixed bed reactor fixed with sulfurized palladium on alumina catalyst such as a SHU) in an up-flow direction at a rate of 1,000 grams/hour. Hydrogen (mixed with methane) was also injected into the reactor at a rate of 17.0 grams/hour. The temperature was 55° C. at the inlet and rises to about 100° C. at the reactor outlet. The effluent was then flowed into a second hydroisomerization reactor (a fixed bed reactor) with the same catalyst operating in a downflow direction essentially isothermally at 75° C. to finish the reaction. After the excess hydrogen and methane were removed the composition of effluent from the second reactor was 6.9 pbw iso- and normal butanes, 27.5 pbw isobutylene, 0 pbw 1-butene, 65.7 pbw (cis and trans)-2-butene, and 0 pbw 1,3-butadiene, indicating that all 1-butene and 1,3-butadiene had been converted to 2-butene.

A fractionation column was operated such that the iso- and normal-butylenes are separated and rejected from the process, and the isobutylene was separated. The 2-butene bottom stream from the fractionation column, comprising >99 pbw 2-butene, was continuously fed to a fixed bed isomerization reactor fixed with the proton form of a borated zeolite catalyst operated at a WHSV of 1.5 h$^{-1}$ at an isothermal temperature of 450° C. The conversion of 2-butene was about 49% with a selectivity to isobutylene of 73% to give an isobutylene yield of 36% per pass. The effluent from the isomerization reactor was recycled to the hydroisomerization reactor. The overall yield of isobutylene based on the total of the C4 olefins (isobutylene, 1,3-butadiene, 1-butene, and (cis/trans)-2-butene) contained in the steam cracker crude C4 stream was determined to be 100%. Overall, this example shows that unlike state-of-the-art technologies, embodiments described herein enable the conversion of a CC4 naphtha steam cracker effluent to isobutylene.

Example 4

Example Process for Forming Isobutylene: Conversion of Crude C4 from Ethane Steam Cracker to Isobutylene There is no existing method for converting CC4 from an ethane steam cracker to isobutylene. Instead, some state-of-the-art technologies include hydroisomerization of 1,3-butadiene to 2-butene but no isomerization of 2-butene to isobutylene. Other state-of-the-art technologies include conversion of all butylenes in a raffinate-1 stream to isobutylene, but no butadiene is contained in the raffinate-1 stream. Other state-of-the-art technologies include isomerizing 1-butene to 2-butene to aid in isobutylene separation but no isomerization step to generate more isobutylene.

For this example of the present disclosure, an effluent from a steam cracker (ethane steam cracker) was separated to obtain a crude C4 (CC4) feed that was used as the C4 feed for forming isobutylene. Table 4 shows the composition of the CC4 feed used for forming isobutylene in this example.

TABLE 3

Typical CC4 Feed Composition

| Components of CC4 Feed | Parts by weight (pbw) of the CC4 Feed |
|---|---|
| iso- and normal butanes | 14.2 |
| isobutylene | 0 |
| 1-butene | 11.1 |
| 2-butenes (cis and trans) | 5.5 |
| 1,3-butadiene | 69.4 |
| Total | 100.2 |

The CC4 feed was continuously introduced to a hydroisomerization reactor (a fixed bed reactor fixed with sulfurized palladium on alumina catalyst such as a SHU) in an up-flow direction at a rate of 1,000 grams/hour. Hydrogen (mixed with methane) was also injected into the reactor at a rate of 16.4 grams/hour. The temperature is 53° C. at the inlet and rises to about 98° C. at the reactor outlet. The effluent then flows into a second hydroisomerization reactor (a fixed bed reactor) with the same catalyst operating in a downflow direction essentially isothermally at 75° C. to finish the reaction. After the excess hydrogen and methane were removed, the composition of effluent from the second reactor is 14.2 pbw iso- and normal butanes, 0 pbw isobutylene, 0 pbw 1-butene, 85.8 pbw (cis/trans)-2-butene and 0 pbw 1,3-butadiene.

A fractionation column was operated such that the iso and normal butylenes are separated and rejected from the process. The 2-butene bottom stream from the fractionation column, comprising >99 pbw 2-butene, was continuously fed to a fixed bed isomerization reactor fixed with the proton form of a modified zeolite catalyst operated at a weight hourly space velocity (WHSV) of 2.5 $h^{-1}$ at an isothermal temperature of 450° C. The conversion of 2-butene was 45% with a selectivity to isobutylene of 75% to give an isobutylene yield of 34% per pass. The effluent from the isomerization reactor was recycled to the hydroisomerization reactor. The overall yield of isobutylene based on the total of the C4 olefins (1,3-butadiene, 1-butene, and (cis/trans)-2-butene) contained in the steam cracker crude C4 stream is 100%. Overall, this example shows that unlike state-of-the-art technologies, embodiments described herein enable the conversion of a CC4 ethane steam cracker effluent to isobutylene.

EMBODIMENTS LISTING

The present disclosure provides, among others, the following embodiments, each of which can be considered as optionally including any alternate embodiments:

Clause A1. A process for forming isobutylene, the process comprising:
hydroisomerizing 1,3-butadiene present in a C4 feed to form a hydroisomerization product effluent comprising isobutylene and 2-butene; and
forming an isobutylene feed by separating the isobutylene from the hydroisomerization product effluent.

Clause A2. The process of Clause A1, further comprising:
separating the 2-butene from the hydroisomerization product effluent;
isomerizing at least a portion of the 2-butene that is separated from the hydroisomerization product effluent to form an isomerization product effluent comprising normal butylenes and isobutylene; and
hydroisomerizing the isomerization product effluent.

Clause A3. The process of any one of Clause A1 or Clause A2, wherein the C4 feed comprises greater than 3 wt % of the 1,3-butadiene based on a total wt % of the C4 feed.

Clause B1. A process for forming polyisobutylene, the process comprising:
hydroisomerizing a C4 feed comprising 1,3-butadiene in a hydroisomerization reactor to form a hydroisomerization product effluent comprising isobutylene and 2-butene;
separating the isobutylene from the hydroisomerization product effluent to form a first isobutylene-containing feed;
forming a reaction mixture comprising a polymerization catalyst and the first isobutylene-containing feed; and reacting the reaction mixture, in a polymerization reactor, to form a polymerization product effluent comprising polyisobutylene (PIB).

Clause B2. The process of Clause B1, further comprising:
separating solid catalyst from the polymerization product effluent to form a filtrate comprising the PIB; and then
introducing the separated solid catalyst to a catalyst preparation unit.

Clause B3. The process of Clause B2, further comprising:
removing isobutane and unreacted isobutylene from the filtrate comprising the PIB to form a C4 separated effluent comprising the PIB.

Clause B4. The process of Clause B3, further comprising (a), or (b1)-(b3), or (c) combinations thereof:
(a) introducing the unreacted isobutylene to the polymerization reactor to polymerize the unreacted isobutylene; or (b1) removing isobutylene oligomer byproducts (e.g., C20 or lower, such as C8-C20) from the C4 separated effluent;
(b2) cracking the isobutylene oligomer byproducts (e.g., C20 or lower, such as C8-C20) to form a second isobutylene-containing feed; and
(b3) introducing the second isobutylene-containing feed to the polymerization reactor to polymerize isobutylene present in the second isobutylene-containing feed; or
(c) combinations thereof.

Clause B5. The process of any one of Clauses B1-B4, further comprising:
separating the 2-butene from the hydroisomerization product effluent; and
isomerizing at least a portion of the 2-butene that is separated from the hydroisomerization product effluent to form an isomerization product effluent comprising normal butylenes and isobutylene.

Clause B6. The process of Clause B5, further comprising hydroisomerizing the isomerization product effluent.

Clause B7. The process of Clause B5, wherein the process further comprises:
oligomerizing isobutylene present in the isomerization product effluent to form isobutylene oligomers;
separating the normal butylenes from the isobutylene oligomers;
cracking the isobutylene oligomers to form a third isobutylene-containing feed; and
introducing the third isobutylene-containing feed to the polymerization reactor to polymerize isobutylene present in the third isobutylene-containing feed to PIB.

Clause B8. The process of any one of Clauses B1-B7, wherein the C4 feed comprises:
the 1,3-butadiene and one or more C4 olefins different from the 1,3-butadiene; or
the 1,3-butadiene as the only C4 olefin present in the C4 feed.

Clause B9. The process of Clause B8, wherein at least a portion of the 1,3-butadiene is converted to the PIB.

Clause B10. The process of any one of Clauses B1-B9, wherein the C4 feed comprises the 1,3-butadiene and one or more of 1-butene, cis-2-butene, trans-2-butene, or combinations thereof.

Clause B11. The process of Clause B10, wherein at least a portion of the 1,3-butadiene is converted to the PIB.

Clause B12. The process of any one of Clauses B1-B11, wherein the C4 feed comprises a crude C4 (CC4) stream that is produced from a steam cracker used to make light hydrocarbon olefins.

Clause B13. The process of Clause B12, wherein a steam cracker feed to the steam cracker comprises butanes, hexanes, naphtha, or combinations thereof.

Clause B14. The process of any one of Clause B12 or Clause B13, wherein the steam cracker feed to the steam cracker comprises ethane.

Clause B15. The process of any one of Clauses B12-B14, wherein the crude C4 stream that is produced from the steam cracker comprises 1,3-butadiene, isobutylene, normal butylene (1-butene, cis and/or trans-2-butene), or combinations thereof.

Clause B16. The process of Clause B15, wherein the crude C4 stream that is produced from the steam cracker comprises about 3 wt % or more of 1,3-butadiene based on a total wt % of the crude C4 stream, such as about 30 wt % or more of 1,3-butadiene, such as from about 50 wt % or more of 1,3-butadiene.

Clause B17. The process of any one of Clauses B1-B16, wherein, prior to the forming the reaction mixture comprising the polymerization catalyst and the first isobutylene-containing feed, the process further comprises:
mixing the first isobutylene-containing feed with a C4 olefin-containing stream that is different from the first isobutylene-containing feed to form an HR-PIB grade stream having an isobutylene content greater than 50 wt % based on a total wt % of the HR-PIB grade stream, wherein the C4 olefin-containing stream that is different from the first isobutylene-containing feed has an isobutylene content of less than 50 wt %.

Clause B18. The process of Clause B17, wherein the C4 olefin-containing stream that is different from the first isobutylene-containing feed comprises raffinate-1.

Clause B19. The process of any one of Clauses B1-B18, wherein the C4 feed comprises tert-butyl alcohol.

Clause B20. The process of any one of Clauses B1-B19, wherein the polymerization reactor comprises a tubular loop reactor employing a circulation loop independent of a feed flow of the first isobutylene-containing feed to the polymerization reactor such that a velocity of the reaction mixture in the tubular loop reactor is about 3 ft/sec (about 0.9 m/sec) or more, such as about 6 ft/sec (about 1.8 m/sec) or more.

Clause B21. The process of Clause B20, wherein a Reynolds number of the reaction mixture polymerized is about 2,000 or more.

Clause B22. The process of any one of Clause B20 or Clause B21, wherein a ratio of a circulation flow of the reaction mixture to the feed flow of the first isobutylene-containing feed is from about 10:1 to about 50:1.

Clause B23. The process of any one of Clauses B1-B22, wherein the reacting the reaction mixture is performed for about 4 minutes or less, such as about 2 minutes or less.

Clause B24. The process of any one of Clauses B1-B23, wherein the PIB comprises:
a first portion comprising polymer chains having alpha vinylidene groups;
a second portion comprising polymer chains having beta vinylidene groups;
a third portion comprising polymer chains having internal vinylidene groups;
the first portion is greater than about 75 wt % based on a total wt % of the PIB, the total wt % of the PIB is equal to 100 wt %; and
a total of the second portion plus the third portion is about 25 wt % or less based on the total wt % of the PIB.

Clause B25. The process of any one of Clauses B1-B24, wherein the PIB is a mid-range vinylidene PIB comprising:
a first portion comprising polymer chains having alpha vinylidene groups;
a second portion comprising polymer chains having internal vinylidene groups; and
the first portion is less than 75 wt % of the mid-range vinylidene PIB based on a total wt % of the mid-range vinylidene PIB, the total wt % of the mid-range vinylidene PIB is equal to 100 wt %;

Clause B26. The process of any one of Clauses B1-B25, wherein the polymerization catalyst comprises a stable, solid BF$_3$ complex.

Clause B27. The process of any one of Clauses B1-B26, wherein after the reacting the reaction mixture, the process further comprises removing the polymerization catalyst from the polymerization product effluent by filtration, centrifugation, any other suitable solid-liquid separation process, or combinations thereof.

Clause B28. The process of any one of Clauses B1-B27, wherein at least a portion of the polymerization catalyst is recycled or otherwise recovered.

Clause C1. A process for forming polyisobutylene, the process comprising:
  hydroisomerizing a C4 feed in a hydroisomerization reactor to form a hydroisomerization product effluent comprising isobutylene and 2-butene;
  separating the isobutylene from the hydroisomerization product effluent to form a first isobutylene-containing feed;
  forming a reaction mixture comprising a polymerization catalyst and the first isobutylene-containing feed;
  reacting the reaction mixture, in a polymerization reactor, to form a polymerization product effluent comprising polyisobutylene (PIB);
  separating the polymerization product effluent into a spent polymerization catalyst and a filtrate comprising the PIB;
  removing isobutane and unreacted isobutylene from the filtrate comprising the PIB to form a C4 separated effluent comprising the PIB;
  introducing the unreacted isobutylene to the polymerization reactor;
  removing isobutylene oligomer byproducts from the C4 separated effluent;
  cracking the isobutylene oligomer byproducts to form a second isobutylene-containing feed;
  introducing the second isobutylene-containing feed to the polymerization reactor;
  separating the 2-butene from the hydroisomerization product effluent;
  isomerizing at least a portion of the 2-butene separated from the hydroisomerization product effluent in an isomerization reactor to form an isomerization product effluent comprising isobutylene and normal butylenes; and
  hydroisomerizing the isomerization product effluent in the hydroisomerization reactor.

Clause C2. The process of Clause C1, further comprising:
  regenerating polymerization catalyst from the spent polymerization catalyst to form a regenerated polymerization catalyst; and
  introducing the regenerated catalyst to the polymerization reactor.

Clause D1. A process for forming polyisobutylene, the process comprising:
  hydroisomerizing a C4 feed in a hydroisomerization reactor to form a hydroisomerization product effluent comprising isobutylene and 2-butene;
  separating the isobutylene from the hydroisomerization product effluent to form a first isobutylene-containing feed;
  forming a reaction mixture comprising a polymerization catalyst and the first isobutylene-containing feed;
  reacting the reaction mixture, in a polymerization reactor, to form a polymerization product effluent comprising polyisobutylene (PIB);
  separating the polymerization product effluent into a spent polymerization catalyst and a filtrate comprising the PIB;
  removing isobutane and unreacted isobutylene from the filtrate comprising the PIB to form a C4 separated effluent comprising the PIB;
  introducing the unreacted isobutylene to the polymerization reactor;
  removing isobutylene oligomer byproducts from the C4 separated effluent;
  cracking the isobutylene oligomer byproducts to form a second isobutylene-containing feed;
  introducing the second isobutylene-containing feed to the polymerization reactor;
  separating the 2-butene from the hydroisomerization product effluent;
  isomerizing at least a portion of the 2-butene separated from the hydroisomerization product effluent in an isomerization reactor to form an isomerization product effluent comprising isobutylene and normal butylenes;
  oligomerizing isobutylene present in the isomerization product effluent to form isobutylene oligomers;
  cracking the isobutylene oligomers to form a third isobutylene-containing feed; and
  introducing the third isobutylene-containing feed to the polymerization reactor Clause D2. The process of Clause D1, further comprising:
  regenerating polymerization catalyst from the spent polymerization catalyst to form a regenerated polymerization catalyst; and
  introducing the regenerated catalyst to the polymerization reactor.

Clause E1. A process for preparing polyisobutylene, comprising:
  supplying a C4 mixture containing 1,3-butadiene and iso and normal butylenes to a selective hydrogenation unit in which the 1,3-butadiene and contained 1-butene is hydroisomerized using a hydroisomerization catalyst to 2-butene;
  supplying the C4 mixture containing 2-butene, and isobutylene, to a fractional distillation column in which the isobutylene is separated;
  supplying the isobutylene and a polymerization catalyst to a polymerization reactor to form a polymerization reaction mixture and thereby producing crude polyisobutylene by a polymerization reaction;
  supplying the crude polyisobutylene to a solids separation unit to:
    remove the polymerization catalyst, which is recycled to a catalyst preparation unit; and
    form a catalyst-free crude polyisobutylene;
  supplying the catalyst-free crude polyisobutylene to a debutanizer column to:
    remove unreacted isobutylene from the catalyst-free crude polyisobutylene and then recycling the unreacted isobutylene to the polymerization reactor; and
    form a debutanized crude polyisobutylene;
  supplying the debutanized crude polyisobutylene to an oligomer strip column in which isobutylene oligomer byproducts up to and including C20 are taken overhead and supplied to an oligomer cracking reactor in which the isobutylene oligomer byproducts are cracked to isobutylene and supplied to a polymerization reactor with a polymerization catalyst thereby producing polyisobutylene; and separating and supplying the 2-butene from the fractional distillation column to a skeletal isomerization reactor in which part of the 2-butene is skeletal isomerized to isobutylene using a skeletal isomerization catalyst to produce a skeletal isomerization mixture; and recycling the skeletal isomerization mixture to the selective hydrogenation unit.

Clause E2. A process for preparing polyisobutylene, comprising:

supplying a C4 mixture containing 1,3-butadiene and iso and normal butylenes to a selective hydrogenation unit in which the 1,3-butadiene and contained 1-butene is hydroisomerized using a hydroisomerization catalyst to 2-butene;

supplying the C4 mixture containing 2-butene, and isobutylene, to a fractional distillation column in which the isobutylene is separated;

supplying the isobutylene and a polymerization catalyst to a polymerization reactor to form a polymerization reaction mixture and thereby producing crude polyisobutylene by a polymerization reaction;

supplying the crude polyisobutylene to a solids separation unit to:
  remove the polymerization catalyst, which is recycled to a catalyst preparation unit; and
  form a catalyst-free crude polyisobutylene;

supplying the catalyst-free crude polyisobutylene to a debutanizer column to:
  remove unreacted isobutylene from the catalyst-free crude polyisobutylene and then recycling the unreacted isobutylene to the polymerization reactor; and
  form a debutanized crude polyisobutylene;

supplying the debutanized crude polyisobutylene to an oligomer strip column in which isobutylene oligomer byproducts up to and including C20 are taken overhead and supplied to an oligomer cracking reactor in which the isobutylene oligomer byproducts are cracked to isobutylene and supplied to a polymerization reactor with a polymerization catalyst thereby producing polyisobutylene;

separating and supplying the 2-butene from the fractional distillation column to a skeletal isomerization reactor in which part of the 2-butene is skeletal isomerized to isobutylene using a skeletal isomerization catalyst to produce a skeletal isomerization mixture;

providing the skeletal isomerization mixture to an oligomerization reactor in which the isobutylene is oligomerized to isobutylene oligomer products in an oligomerization zone, and unreacted normal butylenes are separated in a distillation zone and returned to the selective hydrogenation unit; and supplying the isobutylene oligomer products produced from the skeletal isomerization mixture to a cracking reactor in which the isobutylene oligomer products are cracked to isobutylene and returning the isobutylene to a polymerization reactor with a polymerization catalyst thereby producing polyisobutylene, and after the polymerization reaction all or part of the unreacted isobutylene is recycled back to the polymerization reactor.

Clause E3. The process of any one of Clause E1 or Clause E2, wherein the polymerization reactor is a tubular loop reactor employing a circulation loop independent of a feed flow such that a velocity of a polymerization reaction mixture (comprising the isobutylene and the polymerization catalyst) in reactor tubes of the tubular loop reactor is greater than 3 ft/sec, such as greater than 6 ft/sec.

Clause E4. The process of Clause E3, wherein a Reynolds number of the polymerization reaction mixture polymerized is greater than or equal to 2,000.

Clause E5. The process of Clause E3, wherein a ratio of a circulation flow of the polymerization reaction mixture to the feed flow of the isobutylene is greater than 25:1.

Clause E6. The process of any one of Clause E1 or Clause E2, wherein a reaction time for the polymerization reaction is less than 4 minutes, such as less than 2 minutes.

Clause E7. The process of any one of Clause E1 or Clause E2, wherein the C4 mixture is a CC4 side stream collected from a steam cracker used to make light hydrocarbon olefins.

Clause E8. The process of Clause E7, wherein a feed to the steam cracker is butanes, hexanes or naphtha, or mixtures thereof.

Clause E9. The process of Clause E7, wherein a feed to the steam cracker is ethane.

Clause E10. The process of Clause E7, wherein the CC4 side stream contains 1,3-butadiene, isobutylene, and normal butylenes.

Clause E11. The process of Clause E7, wherein a 1,3-butadiene content of the CC4 side stream is greater than 3%, such as greater than 30%, such as greater than 50%.

Clause E12. The process of any one of Clause E1 or Clause E2, wherein crude polyisobutylene comprises HR-PIB with an alpha vinylidene content greater than or equal to 75%, such as greater than 80%.

Clause E13. The process of any one of Clause E1 or Clause E2, wherein the crude polyisobutylene comprises a mid-range vinylidene polyisobutylene with an alpha vinylidene content of less than 75%, such as less than 65%.

Clause E14. The process of any one of Clause E1 or Clause E2, wherein the polymerization catalyst is a stable solid $BF_3$ complex.

Clause E15. The process of any one of Clause E1 or Clause E2, wherein the polymerization catalyst is removed from the polymerization reaction mixture (comprising the isobutylene and the polymerization catalyst) after the polymerization reaction by filtration, centrifugation, or any other suitable solid-liquid separation processes.

Clause E16. The process of any one of Clause E1 or Clause E2, wherein the polymerization catalyst is all or in part recycled or otherwise recovered.

Clause E17. The process of any one of Clause E1 or Clause E2, wherein the isobutylene separated by the fractional distillation column is mixed with and upgrades a different C4 olefin stream (having an isobutylene content less than 50%) to an HR-PIB grade feed by increasing the isobutylene content to greater than 50%.

Clause E18. The process of Clause E17, wherein the different C4 olefin stream is raff-1.

All documents described herein are incorporated by reference herein, including any priority documents and/or testing procedures to the extent they are not inconsistent with this text. As is apparent from the foregoing general description and the specific embodiments, while forms of the embodiments have been illustrated and described, various modifications may be made without departing from the spirit and scope of the present disclosure. Accordingly, it is not intended that the present disclosure be limited thereby. Likewise, the term "comprising" is considered synonymous with the term "including." Likewise whenever a composition, an element, a group of elements, or a method is preceded with the transitional phrase "comprising," it is understood that we also contemplate the same composition, method, or group of elements with transitional phrases "consisting essentially of," "consisting of," "selected from the group of consisting of," or "Is" preceding the recitation of the composition, element, elements, or method, and vice versa, such as the terms "comprising," "consisting essentially of," "consisting of" also include the product of the combinations of elements listed after the term.

In the foregoing, reference is made to embodiments of the disclosure. However, it should be understood that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the foregoing aspects, features, embodiments and advantages are merely illustrative and are not considered elements or limitations of the appended claims except where explicitly recited in a claim(s). Likewise, reference to "the disclosure" shall not be construed as a generalization of any inventive subject matter disclosed herein and shall not be considered to be an element or limitation of the appended claims except where explicitly recited in a claim(s).

For purposes of this present disclosure, and unless otherwise specified, all numerical values within the detailed description and the claims herein are modified by "about" or "approximately" the indicated value, and consider experimental error and variations that would be expected by a person having ordinary skill in the art. For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. For example, the recitation of the numerical range 1 to 5 includes the subranges 1 to 4, 1.5 to 4.5, 1 to 2, among other subranges. As another example, the recitation of the numerical ranges 1 to 5, such as 2 to 4, includes the subranges 1 to 4 and 2 to 5, among other subranges. Additionally, within a range includes every point or individual value between its end points even though not explicitly recited. For example, the recitation of the numerical range 1 to 5 includes the numbers 1, 1.5, 2, 2.75, 3, 3.80, 4, 5, among other numbers. Thus, every point or individual value may serve as its own lower or upper limit combined with any other point or individual value or any other lower or upper limit, to recite a range not explicitly recited.

As used herein, the indefinite article "a" or "an" shall mean "at least one" unless specified to the contrary or the context clearly indicates otherwise. For example, embodiments comprising "reactor" include embodiments comprising one, two, or more reactors, unless specified to the contrary or the context clearly indicates only one reactor is included.

While the foregoing is directed to embodiments of the present disclosure, other and further embodiments of the disclosure may be devised without departing from the basic scope thereof, and the scope thereof is determined by the claims that follow.

What is claimed is:

1. A process for forming isobutylene, the process comprising:
    (a) hydroisomerizing, in a hydroisomerization unit, 1,3-butadiene present in a feed to a hydroisomerization product effluent comprising 2-butene, the hydroisomerizing the 1,3-butadiene comprising converting at least a portion of the 1,3-butadiene to the 2-butene;
    (b) isomerizing at least a portion of the 2-butene present in the hydroisomerization product effluent to form an isomerization product effluent comprising 1-butene, 2-butene, and isobutylene, the isomerization product effluent having a higher concentration of isobutylene than the concentration of isobutylene in the hydroisomerization product effluent;
    (c) combining the isomerization product effluent with the feed to form a mixture; and
    (d) hydroisomerizing the mixture in the hydroisomerization unit.

2. The process of claim 1, wherein:
    the mixture formed at (c) comprises 1-butene; and
    the hydroisomerizing the mixture at (d) comprises forming 2-butene from the 1-butene present in the mixture.

3. The process of claim 1, wherein, after (c), the process further comprises:
    separating at least a portion of the isobutylene from the mixture.

4. The process of claim 1, wherein the feed comprising the 1,3-butadiene comprises greater than 3 wt % of the 1,3-butadiene based on a total wt % of the feed.

5. The process of claim 1, wherein the feed comprising the 1,3-butadiene comprises an effluent from a steam cracker, a catalytic cracker, or combinations thereof.

6. The process of claim 1, wherein the feed comprising the 1,3-butadiene is free of isobutylene.

7. A process for forming polyisobutylene, the process comprising:
    (a) hydroisomerizing, in a hydroisomerization unit, 1,3-butadiene present in a feed to a hydroisomerization product effluent comprising 2-butene, the hydroisomerizing the 1,3-butadiene comprising converting at least a portion of the 1,3-butadiene to the 2-butene;
    (b) isomerizing at least a portion of the 2-butene present in the hydroisomerization product effluent to form an isomerization product effluent comprising 1-butene, 2-butene, and isobutylene, the isomerization product effluent having a higher concentration of isobutylene than the concentration of isobutylene in the hydroisomerization product effluent;
    (c) combining the isomerization product effluent with the feed to form a mixture;
    (d) hydroisomerizing the mixture in the hydroisomerization unit to form a hydroisomerized mixture; and
    (e) reacting a reaction mixture comprising at least a portion of the isobutylene present in the hydroisomerized mixture formed at (d) and a polymerization catalyst to form a first polymerization product effluent comprising polyisobutylene (PIB).

8. The process of claim 7, wherein, after (c), the process further comprises:
separating the isobutylene from the mixture to form a first isobutylene-containing feed.

9. The process of claim 8, further comprising:
polymerizing isobutylene present in the first isobutylene-containing feed to form a second polymerization product effluent comprising PIB.

10. The process of claim 7, wherein:
the mixture formed at (c) comprises 1-butene; and
the hydroisomerizing the mixture at (d) comprises forming 2-butene from the 1-butene present in the mixture.

11. The process of claim 7, further comprising:
removing unreacted isobutylene from the first polymerization product effluent; and
polymerizing the unreacted isobutylene.

12. The process of claim 7, further comprising:
removing isobutylene oligomer byproducts from the first polymerization product effluent;
cracking the isobutylene oligomer byproducts to form a second isobutylene-containing feed; and
polymerizing isobutylene present in the second isobutylene-containing feed.

13. The process of claim 7, further comprising:
oligomerizing isobutylene present in the isomerization product effluent to form an oligomerization effluent comprising isobutylene oligomers;
cracking the isobutylene oligomers to form a third isobutylene-containing feed; and
polymerizing isobutylene present in the third isobutylene-containing feed to PIB.

14. The process of claim 13, wherein, prior to the cracking the isobutylene oligomers to form the third isobutylene-containing feed, the process further comprises:
separating normal butylenes from the oligomerization effluent.

15. The process of claim 7, wherein the polymerization catalyst comprises a solid polymerization catalyst.

16. The process of claim 15, further comprising:
separating the solid polymerization catalyst from the first polymerization product effluent;
regenerating polymerization catalyst from the separated solid polymerization catalyst; and
polymerizing isobutylene with the regenerated polymerization catalyst.

17. The process of claim 7, wherein the feed comprising the 1,3-butadiene comprises greater than 3 wt % of the 1,3-butadiene based on a total wt % of the feed.

18. The process of claim 7, wherein the feed comprising the 1,3-butadiene comprises an effluent from a steam cracker, a catalytic cracker, or combinations thereof.

19. The process of claim 7, wherein the feed comprising the 1,3-butadiene is free of isobutylene.

* * * * *